(12) United States Patent
Gutierro Aduriz et al.

(10) Patent No.: US 11,007,139 B2
(45) Date of Patent: *May 18, 2021

(54) RISPERIDONE OR PALIPERIDONE IMPLANT FORMULATION

(71) Applicant: Laboratorios Farmacéuticos ROVI, S.A., Madrid (ES)

(72) Inventors: Ibon Gutierro Aduriz, Granada (ES); Guillermo Franco Rodriguez, Madrid (ES)

(73) Assignee: Laboratorios Farmacéuticos ROVI, S.A., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/456,900

(22) Filed: Jun. 28, 2019

(65) Prior Publication Data

US 2019/0321286 A1 Oct. 24, 2019

Related U.S. Application Data

(60) Division of application No. 14/555,287, filed on Nov. 26, 2014, now Pat. No. 10,335,366, which is a continuation-in-part of application No. PCT/EP2013/061320, filed on May 31, 2013, and a continuation-in-part of application No. 13/690,647, filed on Nov. 30, 2012, now Pat. No. 10,085,936, which is a continuation-in-part of application No. PCT/EP2011/059000, filed on May 31, 2011, said application No. 14/555,287 is a continuation-in-part of application No. 13/690,707, filed on Nov. 30, 2012, now Pat. No. 10,058,504, which is a continuation-in-part of application No. PCT/EP2011/059001, filed on May 31, 2011, application No. 16/456,900, which is a continuation of application No. 16/368,258, filed on Mar. 28, 2019, which is a division of application No. 14/555,287, filed on Nov. 26, 2014, now Pat. No. 10,335,366.

(30) Foreign Application Priority Data

| May 31, 2010 | (EP) | ..................................... 10382153 |
| May 31, 2010 | (EP) | ..................................... 10382154 |
| May 31, 2012 | (EP) | ..................................... 12170362 |

(51) Int. Cl.
| *A61K 9/00* | (2006.01) |
| *A61K 31/519* | (2006.01) |
| *A61K 47/34* | (2017.01) |

(52) U.S. Cl.
CPC .......... *A61K 9/0024* (2013.01); *A61K 31/519* (2013.01); *A61K 47/34* (2013.01)

(58) Field of Classification Search
None
See application file for complete search history.

(56) References Cited

U.S. PATENT DOCUMENTS

| 3,636,956 | A | 1/1972 | Schneider |
| 3,773,919 | A | 11/1973 | Boswell |
| 4,389,330 | A | 6/1983 | Tice |
| 4,523,591 | A | 6/1985 | Kaplan |
| 4,530,840 | A | 7/1985 | Tice |
| 4,938,763 | A | 7/1990 | Dunn |
| 5,620,700 | A | 4/1997 | Bergren |
| 5,688,801 | A | 11/1997 | Mesens |
| 5,770,231 | A | 6/1998 | Mesens |
| 6,143,314 | A | 11/2000 | Chandrashekar |
| 6,331,311 | B1 | 12/2001 | Brodbeck |
| 6,528,080 | B2 | 3/2003 | Dunn |
| 6,565,874 | B1 | 5/2003 | Dunn |
| 6,630,155 | B1 | 10/2003 | Chandrashekar |
| 6,673,767 | B1 | 1/2004 | Brodbeck |
| 6,773,714 | B2 | 8/2004 | Dunn |
| 6,803,055 | B2 | 10/2004 | Mesens |
| 7,118,763 | B2 | 10/2006 | Mesens |
| 8,076,448 | B2 | 12/2011 | Moore |
| 8,221,778 | B2 | 7/2012 | Siegel |

(Continued)

FOREIGN PATENT DOCUMENTS

| EP | 2394663 A1 | 12/2011 |
| EP | 2394664 A1 * | 12/2011 | ........... A61K 31/519 |

(Continued)

OTHER PUBLICATIONS

Connelly Clinical Pharmacist, Sep. 2014, vol. 6, No. 7, pp. 1-6. (Year: 2014).*

Risperidone Indications [online], Guzman, Dec. 20, 2013 [retrieved on: Jun. 16, 2018], Retrieved from the internet:<https://psychopharmacologyinstitute.com/publication/risperidone-indications-fda-approved-and-off-label-uses-2124>. (Year: 2013).*

Understanding Unapproved Use of Approved Drugs "Off Label" [online], FDA [retrieved on Jun. 16, 2018], Retrieved from the internet: <https://www.fda.gov/patients/learn-about-expanded-access-and-other-treatment-options/understanding-unapproved-use-approved-drugs-label>. (Year: 2018).*

(Continued)

*Primary Examiner* — Katherine Peebles
(74) *Attorney, Agent, or Firm* — Innovar, L.L.C.; Rick Matos

(57) ABSTRACT

The present invention is directed to an injectable intramuscular depot composition suitable for forming an in situ solid implant in a body, comprising a drug which is risperidone and/or paliperidone or any pharmaceutically acceptable salt thereof in any combination, a biocompatible copolymer based on lactic and glycolic acid having a monomer ratio of lactic to glycolic acid of about 50:50 and DMSO solvent, wherein the composition releases the drug with an immediate onset of action and continuously for at least 4 weeks and wherein the composition has a pharmacokinetic profile in vivo that makes it suitable to be administered each 4 weeks or even longer periods.

49 Claims, 6 Drawing Sheets

(56) References Cited

U.S. PATENT DOCUMENTS

| | | | |
|---|---|---|---|
| 8,324,343 B2 | 12/2012 | Moore | |
| 10,058,504 B2 | 8/2018 | Gutierro Aduriz et al. | |
| 10,085,936 B2 | 10/2018 | Gutierro Aduriz et al. | |
| 10,182,982 B2 | 1/2019 | Gutierro Aduriz et al. | |
| 10,195,138 B2 | 2/2019 | Gutierro Aduriz et al. | |
| 10,285,936 B2 | 5/2019 | Franco Rodriguez et al. | |
| 10,335,366 B2 | 7/2019 | Gutierro Aduriz et al. | |
| 10,350,159 B2* | 7/2019 | Gutierro Aduriz | .. A61K 9/0024 |
| 10,463,607 B2* | 11/2019 | Gutierro Aduriz | .. A61K 31/519 |
| 2002/0009492 A1 | 1/2002 | Truong | |
| 2002/0023409 A1 | 2/2002 | Py | |
| 2003/0165571 A1 | 9/2003 | Mesens et al. | |
| 2004/0010224 A1 | 1/2004 | Bodmeier | |
| 2004/0247870 A1 | 12/2004 | Brown | |
| 2005/0042294 A1 | 2/2005 | Thanoo | |
| 2006/0121085 A1 | 6/2006 | Warren | |
| 2006/0210604 A1 | 9/2006 | Dadey | |
| 2007/0003596 A1 | 1/2007 | Tittelbach | |
| 2007/0077304 A1 | 4/2007 | Luk | |
| 2007/0275068 A1 | 11/2007 | Martens | |
| 2008/0206303 A1 | 8/2008 | Gellert | |
| 2008/0287464 A1 | 11/2008 | Wright | |
| 2009/0264491 A1 | 10/2009 | McKay | |
| 2009/0305957 A1 | 12/2009 | Moore | |
| 2010/0015195 A1 | 1/2010 | Jain | |
| 2010/0021544 A1 | 1/2010 | Bourges | |
| 2010/0266655 A1 | 10/2010 | Dadey | |
| 2010/0292195 A1 | 11/2010 | Dadey | |
| 2012/0108511 A1 | 5/2012 | Moore | |
| 2015/0147398 A1 | 5/2015 | Gutierro Aduriz et al. | |
| 2015/0150791 A1 | 6/2015 | Gutierro Aduriz et al. | |
| 2019/0117554 A1 | 4/2019 | Gutierro Aduriz et al. | |
| 2019/0151230 A1 | 5/2019 | Gutierro Aduriz et al. | |

FOREIGN PATENT DOCUMENTS

| | | |
|---|---|---|
| WO | WO 99/036071 A1 | 7/1999 |
| WO | WO 02/038185 A2 | 5/2002 |
| WO | WO 2007/041410 | 4/2007 |
| WO | WO 2008/059058 | 5/2008 |
| WO | WO 2008/153611 | 12/2008 |
| WO | WO2009/060473 | 5/2009 |
| WO | WO 2009/060473 A1 | 5/2009 |
| WO | WO 2011/151355 A1 | 12/2011 |
| WO | WO 2011/151356 A1 | 12/2011 |
| WO | WO 2013/178811 A1 | 12/2013 |
| WO | WO 2013/178812 A1 | 12/2013 |
| WO | WO 2014/019972 A1 | 2/2014 |

OTHER PUBLICATIONS

SIGM-ALDRICH (Dimethly sulfoxide [online]. Sigma-Aldrich, Jan. 12, 2009. <URL:http://www.sigmaaldrich.com/chemistry/solvents/dimethyl-sulfoxide-center.html>.

Product Book. Risperidone [online]. Santa Cruz Biotechnology (2014). <URL:http://www.scbt.com/datasheet-204881-risperidone.html>.

Wang et al. ("Design of a long-term antipsychotic in situ forming implant and its release control method and mechanism", Int. J. Pharm., May 10, 2012;427(2):284-92).

Maryott et al. (Table of Dielectric Constants of Pure Liquids, National Bureau of Standards, Circular No. 514, Aug. 10, 1951).

Gouw et al. (Physical Properties of Triglycerides IV. Dielectric Constant, Fette Seifen Anstrichmittel, (1967), 69(4), 223-226).

Lide (Properties of Common Laboratory Solvents, CRC Handbook of Chemistry and Physics 84th Ed., 2003-2004, Sect. 15-14, CRC Press, New York).

* cited by examiner

RISPERIDONE OR PALIPERIDONE IMPLANT FORMULATION

CROSS-REFERENCE TO EARLIER FILED APPLICATIONS

The present application claims the benefit of and is a continuation of application Ser. No. 16/368,258 filed Mar. 28, 2019, which is a divisional of application Ser. No. 14/555,287 filed Nov. 26, 2014, which is a continuation-in-part of application No. PCT/EP2013/061320, filed May 31, 2013, which claims the benefit of application No. EP 12170362.3 filed May 31, 2012, and said application Ser. No. 14/555,287 is also a continuation-in-part of application Ser. No. 13/690,647 filed Nov. 30, 2012, now U.S. Pat. No. 10,085,936 issued Oct. 2, 2018, which is a continuation-in-part of application No. PCT/EP2011/059000, filed May 31, 2011, which claims the benefit of application No. EP 10382154.2 filed May 31, 2010, and said application Ser. No. 14/555,287 also a continuation-in-part of Ser. No. 13/690,707, filed Nov. 30, 2012, now U.S. Ser. No. 10,058,504 issued Aug. 28, 2018, which is a continuation-in-part of application No. PCT/EP2011/059001, filed May 31, 2011, which claims the benefit of application No. EP 10382153.4 filed May 31, 2010, and the present application is also a divisional of application Ser. No. 14/555,287 filed Nov. 26, 2014, the entire disclosures of which are hereby incorporated by reference.

FIELD OF THE INVENTION

The present invention relates to extended release pharmaceutical compositions for intramuscular injection comprising the drug risperidone, its pharmaceutically acceptable salts and/or its metabolites like as paliperidone, wherein the composition releases the drug with an immediate onset of action and continuously for at least 4 weeks, and wherein the composition has a pharmacokinetic profile in vivo that makes it suitable to be administered each 4 weeks or even longer periods. Specifically, the present invention is related to compositions for injectable in-situ forming biodegradable implants comprising risperidone and/or paliperidone.

BACKGROUND OF THE INVENTION

Risperidone and paliperidone are atypical antipsychotic drugs with benzisoxazole and piperidine functional groups, which act as strong dopaminergic antagonist and selective serotonin receptor antagonist. Risperidone is FDA approved for the treatment of schizophrenia since 1993. It is the only drug presently approved for the treatment of schizophrenia in young people under 18 years, and together with lithium, for the treatment of bipolar disorders in children/youth ages between 10-18 years old. Conventional risperidone therapy of schizophrenia involves daily oral tablets, although it is also available as a solution and orally disintegrating tablets.

In fact, one of the intrinsic problems that risperidone or paliperidone-targeted patients usually face is the dissociation of some schizophrenic patients from the treatment, moreover when it consists of a daily medication, leading to irregular or inconstant treatments and favoring the appearance of psychotic crisis. Moreover, this kind of therapy gives rise to high differences in the plasma levels (measured as the difference between Cmax and Cmin) in patients, therefore usually affecting the patient's mood.

Risperidone and paliperidone are therefore good drug candidates for incorporation into sustained delivery devices, where the patients would be covered or treated for long time periods with just one dose and without the need of caregivers to pay attention to a daily medication, and where more homogeneous plasma levels in the patient are desirable. Other indications may involve bipolar mania and schizoaffective disorder, and its possible use in autism and Asperger's syndrome and Tourette's disorder may be of benefit to the patients.

Risperidone was initially marketed as Risperdal® and recently became generic. Currently, the long-acting injectable risperidone formulation, Risperdal Consta®, is the first depot atypical antipsychotic drug in the market. It is an intramuscular risperidone-containing PLGA microparticles formulation and is intended to deliver therapeutic levels of risperidone by bi-weekly administrations. However, due to the inherent lag phase of most microparticle based products, the patient is required to supplement the first weeks with daily doses of oral risperidone after first administration. Approximately three weeks after a single intramuscular injection of Risperdal Consta® and concurrent daily doses of oral risperidone, the microspheres release sufficient risperidone in the systemic circulation that the patient can discontinue supplementation with daily doses of the oral therapy. However, this period of oral supplementation could be a risk factor of non-compliance. Also, the presence on the body of two doses at the same time could be a potential risk of adverse events, such as irregular formulation behaviour and toxicity.

Paliperidone recently received marketing approval as the first oral atypical antipsychotic with an extended release, which is achieved by an osmotic-controlled release oral delivery system. Paliperidone ER (WO2006/17537) is marketed as Invega Sustenna® and unsaturated derivatives thereof are described in WO2008/128436. Other extended release oral dosage forms for paliperidone are under development. Due the presence of a secondary hydroxyl group, paliperidone may be provided as a prodrug. WO2009/15828 details acid-labile low molecular weight prodrugs of paliperidone intended to undergo hydrolysis in the stomach.

Therefore, in view of the state of the art, it is of interest to develop very long-acting, injectable depots of risperidone and/or paliperidone. There is great need to improve the compliance factor particularly in the treatment of schizophrenia. The development of once-weekly or even longer acting injectable depot formulations of those drugs will mark a significant step forward to ensure continuous and steady supply of the effective medication. In U.S. Pat. No. 5,965,168 application is described compounds of formula I which are formulated in sustained release microparticles. Risperidone is mentioned as the preferred compound and risperidone is used as basis for all experiments therein. FIG. 5 therein shows the plasma concentration time curves for the active moiety (sum of risperidone and paliperidone) after intramuscular injection of risperidone depot.

WO2008/153611 describes sustained release formulations of risperidone and metabolites. Here, risperidone is mixed with a soluble thermoplastic polymer, forming an encapsulating residue upon injection from which risperidone is slowly released. EP2234617 reveals ester-linked prodrugs of paliperidone. The substance paliperidone palmitate is approved as a once-monthly atypical antipsychotic intramuscular injection for treating schizophrenia and preventing recurrence of its symptoms. Paliperidone palmitate is formulated in a submicrocrystalline form. Paliperidone palmitate due to its dissolution rate-limited absorption exhibits flip-flop kinetics, where the apparent half-life is controlled by the absorption rate constant. Additionally the volume of injected drug product also impacts the apparent rate constant. It was also discovered that deltoid injections result in a faster rise in initial plasma concentration, facilitating a rapid attainment of potential therapeutic concentrations. Consequently, to facilitate patients' attaining a rapid therapeutic concentration of paliperidone it is preferred to provide the initial loading dose of paliperidone palmitate in the deltoids. The loading dose should be from about 100 mg-eq. to about 150 mg-eq. of paliperidone provided in the form of paliperidone palmitate. After the first or more preferably after the second loading dose injection patients will be approaching a steady state concentration of paliperidone in their plasma and may be injected in either the deltoid or the gluteal muscle thereafter. However, it is preferred that the patients receive further injections in the gluteal muscle. US2009/163519 outlines corresponding dosing regimen for long-acting injectable paliperidone esters of the palmitate type.

Other antipsychotic depot medications are also characterized by the need for concomitant oral medication or booster injections in order to obtain desired plasma levels of the active drug. For example, Risperdal Consta® requires oral antipsychotic treatment during the initiation phase.

Other depot formulation is described by the international application WO2011/42453. This specification describes a pharmaceutical composition for subcutaneous injection comprising a paliperidone compound. In particular the composition refers to a composition in which paliperidone is linked by an ester bondage to a hydrogel. The formulation releases paliperidone by ester bondage cleavage and claims to release the paliperidone with an immediate onset of action and for an extended release time. Moreover, this specification relates to a pharmaceutical composition for subcutaneous injection comprising a paliperidone compound in a certain concentration.

Finally, another antipsychotic injectable depot composition is described in the international application number WO2011/151355. This application is directed to a composition that can be used to deliver an antipsychotic drug such as risperidone as an injectable in-situ forming biodegradable implant for extended release providing therapeutic plasma levels from the first day. The composition is in the form of drug suspension on a biodegradable and biocompatible copolymer or copolymers solution using water miscible solvents that is administered in liquid form. Once the composition contacts the body fluids, the polymer matrix hardens retaining the drug, forming a solid or semisolid implant that releases the drug in a continuous manner.

SUMMARY OF THE INVENTION

Therefore, the compositions already described in the state of the art do not meet the existing needs in risperidone and or paliperidone compositions, kits and treatments for psychiatric disorders, and there still exists a need of compositions and devices to allow a controlled, constant release of the drug during prolonged periods of time during at least 4 weeks without a concomitant treatment or initial doses of risperidone and/or paliperidone.

Aspects of the invention provide an injectable depot composition, a kit for use in preparing the composition, a method of administering the composition, a method of preparing the composition, and a method of treating a disease or disorder with the composition. The method of administering can be used as a method of treating. The disease or disorder is therapeutically responsive to risperidone and/or paliperidone.

The invention provides an injectable intramuscular depot composition suitable for forming an in situ solid implant in a body, the composition comprising a drug which is risperidone and/or paliperidone, or its pharmaceutically acceptable derivatives and/or salts in any combination thereof, a biocompatible copolymer based on lactic and glycolic acid having a monomer ratio of lactic to glycolic acid in the range of 45:55 to 55:45, 48:52 to 52:48 or about 50:50, i.e. 50:50±10%, and DMSO, wherein the composition releases the drug with an immediate (or rapid) onset of action and continuously for at least 4 weeks and wherein the composition has a pharmacokinetic profile in vivo with substantially no or with minimal burst release of the drug characterised in that the biocompatible copolymer has a molecular weight between 30 and 46 and preferably between 30 and 36 kDa and has an inherent viscosity in the range of 0.26-0.31 and preferably between 0.26-0.29 dl/g±10%.

The invention provides a pharmaceutical kit suitable for in situ formation of a biodegradable non-particulate solid implant in a subject in need thereof. In some embodiments, the kit comprises: a first container comprising drug, and/or a metabolite and/or a prodrug thereof; a second container comprising a biocompatible PLGA copolymer having an inherent viscosity in the range of about 0.26-0.31 dl/g or about 0.26-0.29 dl/g; and a third container comprising DMSO. By mixing the contents of the third container with the contents of the second container, a polymeric solution is formed, which solution is then mixed with the contents of the first container to form the injectable composition as described herein. In some embodiments, the copolymer and drug (and/or a metabolite and/or a prodrug thereof) are included in a first container, and DMSO is included in a second container. In some embodiments, the containers are syringes and the mixing of their contents may be performed by direct or indirect connection followed by moving the plungers of the syringes forwards and backwards. Embodiments of the invention include those wherein: a) drug and/or copolymer is present in solid form in a container prior to mixing with the solvent; or b) drug and/or copolymer is present in particulate form or as a lyophilisate in a container prior to mixing with the solvent (DMSO).

The invention includes a method of administering the injectable composition, comprising: a) administering an amount of sustained release injectable depot composition comprising a dose of drug, metabolite and/or derivative thereof; and b) after about 4 weeks, about 5 weeks, or about 6 weeks, from the prior dose, administering an amount of sustained release injectable depot composition comprising a dose of drug, metabolite and/or prodrug thereof. The invention comprises embodiments wherein step b) is repeated one or more times.

The invention also includes a method of treating a disease or disorder that is therapeutically responsive to risperidone and/or paliperidone and/or a prodrug thereof, the method comprising: a) administering to a subject in need thereof an amount of sustained release injectable depot composition comprising a dose of drug, metabolite and/or derivative thereof; and b) after about 4 weeks, about 5 weeks, or about 6 weeks, from the prior dose, administering to the subject an amount of sustained release injectable depot composition comprising a dose of drug, metabolite and/or prodrug thereof. The invention comprises embodiments wherein step b) is repeated one or more times.

The period of time from one dose administration to another is a dosing period. A treatment period comprises plural dosing periods.

The invention includes all combinations of aspects, embodiments and sub-embodiments disclosed herein.

DETAILED DESCRIPTION OF THE INVENTION

Figure 1:
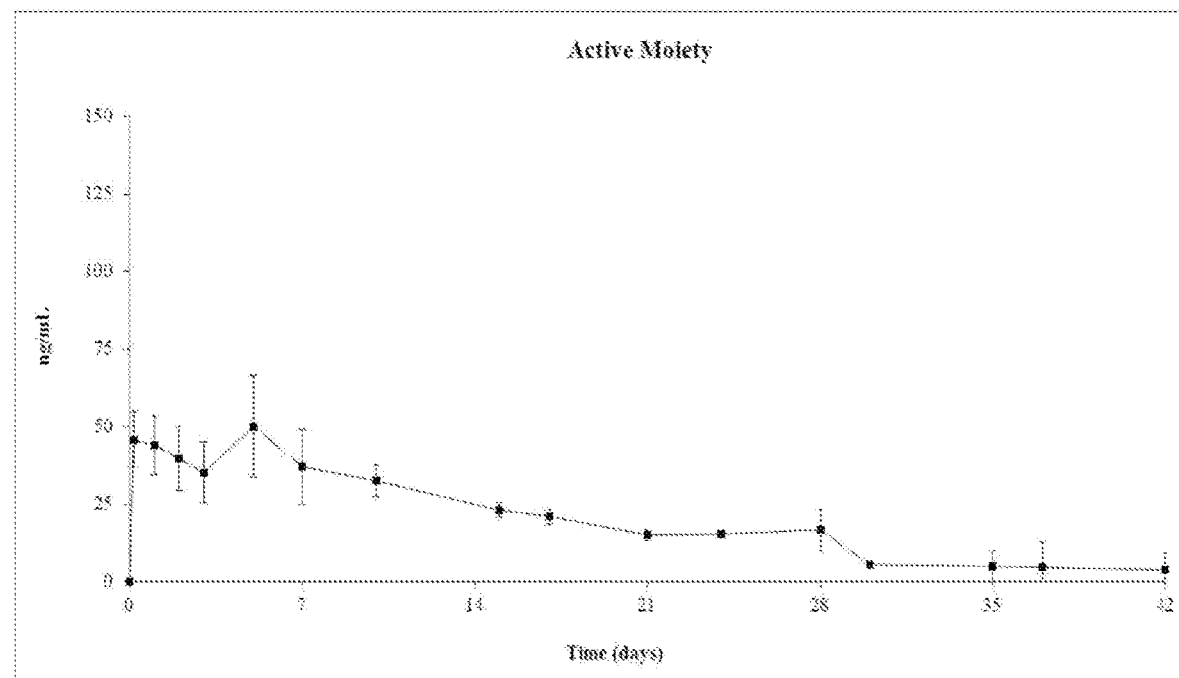
FIG. 1.—Active moiety levels profile in dog after the administration of the risperidone formulation described in example 1 to Beagle dogs (n=3). Dose is 2.5 mg/kg. Results are expressed as ng/ml plasma values of active moiety versus time. The table describes Area Under the Curve (AUC) of active moiety plasma levels versus time. AUC all as well as AUC vs three different time frames are included. Units are expressed in h*ng/ml.

Unless otherwise specified, the term drug, metabolite and prodrug thereof are used interchangeably. In general, the term drug encompasses a metabolite and prodrug thereof.

As used herein and unless otherwise specified, the drug or active ingredient included in the injectable composition can be present in free base, salt, amorphous, crystalline, anhydrous, hydrate, optically pure, optically enriched or racemic forms thereof. Combinations of these various forms are also within the scope of the invention. A prodrug, metabolite or derivative of the drug can also be included.

In some embodiments, the salt forms of risperidone can be made according to U.S. Publication No. 20040266791, the relevant disclosure of which is hereby incorporated by reference; however, other known salts can be used. Since paliperidone and risperidone share substantial structural similarity, salts of paliperidone can be made as described for salts of risperidone.

As used herein, the term "prodrug" is taken to mean a compound that is administered in an inactive (or less than fully active) form, and is subsequently converted to an active pharmacological agent through normal metabolic processes. A prodrug serves as a type of 'precursor' to the intended drug, e.g. risperidone, paliperidone, or other drug.

As used herein, the term "derivative" is taken to mean a compound that is obtained by chemical modification of a parent compound such that the "derivative" includes within it almost all or all of the chemical structure of the parent (or base) compound. A derivative is a compound that is formed from a similar compound or a compound that can be imagined to arise from another compound, if one atom is replaced with another atom or group of atoms. A derivative is a compound derived or obtained from another and containing essential elements of the parent substance. A derivative is a chemical compound that may be produced from another compound of similar structure in one or more steps.

As used herein, the term "polymeric solution" is taken to mean the fluid composition comprising a combination of the solvent and the polymer dissolved therein. In some embodiments, at least 80%, at least 90%, at least 95%, at least 99% or all of the polymer is dissolved in the solvent. If not otherwise specified, the viscosity value of the polymeric solution or the injectable composition is given in Pa·s units.

The compositions of the invention comprise at least a polymer or polymer matrix, a solvent and a drug.

The composition and kit, used to prepare the composition, are provided with a polymer or copolymer that is soluble in a solvent, which is non-toxic and water miscible, to form a liquid polymer solution, in which the drug is included. When the implantable compositions are exposed to body fluids or water, the solvent (DMSO) diffuses away from the polymer-drug mixture and water diffuses into the mixture where it coagulates the polymer thereby trapping or encapsulating the drug within the polymeric matrix as the composition solidifies into a single implant at the injection site. The release of drug follows the general characteristics for diffusion or dissolution of a drug from within a polymeric matrix. Drug is also released by polymer erosion/degradation. The drug (active ingredient) forms a suspension or dispersion within a biodegradable and biocompatible polymeric solution to form an injectable composition that can be administered by way of a syringe (or pump) and a needle. The composition solidifies inside the body by solvent diffusion, thereby forming the single implant at the site of injection.

The polymer or polymer matrix is preferably a biocompatible and biodegradable polymer matrix. In order not to cause any severe damage to the body following administration, the preferred polymers are biocompatible, non-toxic for the human body, not carcinogenic, and do not induce significant tissue inflammation. The polymers are preferably biodegradable in order to allow natural degradation by body processes, so that they are readily disposable and do not accumulate in the body. The preferred polymeric matrices in the practice in this invention are selected from end-capped terminal carboxylic poly-lactide and poly-glycolic acid copolymers, e.g. poly(lactic acid-co-glycolic acid) copolymer (PLGA copolymer), mixed in a ratio ranging from 45:55 to 55:45 or 48:52 to 52:48, and preferably of about 50:50, i.e. 50:50±10%, with an average molecular weight in the range of 30-45 and preferably in the range of 30-36 KDa, and an inherent viscosity preferably in the range of 0.25-0.31 and more preferably in the range of 0.26-0.29 dl/g±10%. The expression "about 50:50" as used in this description, refers to a monomer ratio of lactic to glycolic acid of biocompatible copolymer based on lactic and glycolic acid as applied in the context of the invention for a monomer ratio measure with an standard technical error (standard deviation) of ±10%. The commercially available grades of PLGA copolymer are known to vary slightly in their actual ratio of monomers even though they may be listed as having a 50:50 monomer ratio. For example, a copolymer specified as having a monomer ratio of 50:50 may actually have a monomer ratio ranging from 45:55 to 55:45 or 48:52 to 52:48. Accordingly, whenever the monomer ratio of "50:50" or "about 50:50" is specified herein, all ratios ranging from 45:55 to 55:45 are considered as being interchangeable therewith.

Inherent viscosity can be measured in chloroform at 25° C. at a concentration of 0.1% wt/v with a Ubbelhode size 0c glass capillary viscometer (RESOMER® grades) or in chloroform at 30° C. and at a concentration of 0.5% wt/v with a size 25 Cannon-Fenske glass capillary viscometer (LAKESHORE MATERIALS™ grades). Suitable grades of PLGA copolymers as described herein (according to molecular weight, intrinsic viscosity and/or molar ratio of lactic acid monomer to glycolic acid monomer) are end-capped (such as with an ester group, e.g. lauryl ester, methyl ester) are available from EVONIK® (Essen, Germany), Boehringer Ingelheim (Ingelheim am Rhein, Germany), ALKERMES (Dublin, Ireland) or SIGMA ALDRICH (ST. Louis, Mo.) and are marketed under the tradenames RESOMER®, LAKESHORE BIOMATERIALS™, or MEDISORB®. As the composition of some grades of end-capped PLGA is proprietary, the identity of the ester end-cap is not publicly available. Nonetheless, the performance properties of the grades of PLGA copolymer described herein are known and are used to characterize the material.

For the purpose of the present invention, throughout the present specification the term intrinsic or inherent viscosity $(\eta_{inh})$ of the polymer is defined as the ratio of the natural logarithm of the relative viscosity, $\eta_r$, to the mass concentration of the polymer, c, i.e.:

$$\eta_{inh} = (ln\ \eta_r)/c$$

and the relative viscosity $(\eta_r)$ is the ratio of the viscosity of the solution q to the viscosity of the solvent $\eta_s$, i.e.:

$$\eta_r = \eta/\eta_s$$

If not otherwise specified, the intrinsic viscosity and molecular weight values throughout the present specification are to be understood as measured with the method explained in example 1. The value of intrinsic viscosity is considered in the present specification, as commonly accepted in the art, as an indirect indicator of the polymer molecular weight. In this way, a reduction in the intrinsic viscosity of a polymer, measured at a given concentration in a certain solvent, with same monomer composition and terminal end groups, is an indication of a reduction in the polymer molecular weight (IUPAC. Basic definitions of terms relating to polymers 1974. Pure Appl. Chem. 40, 477-491 (1974).

Figure 11:
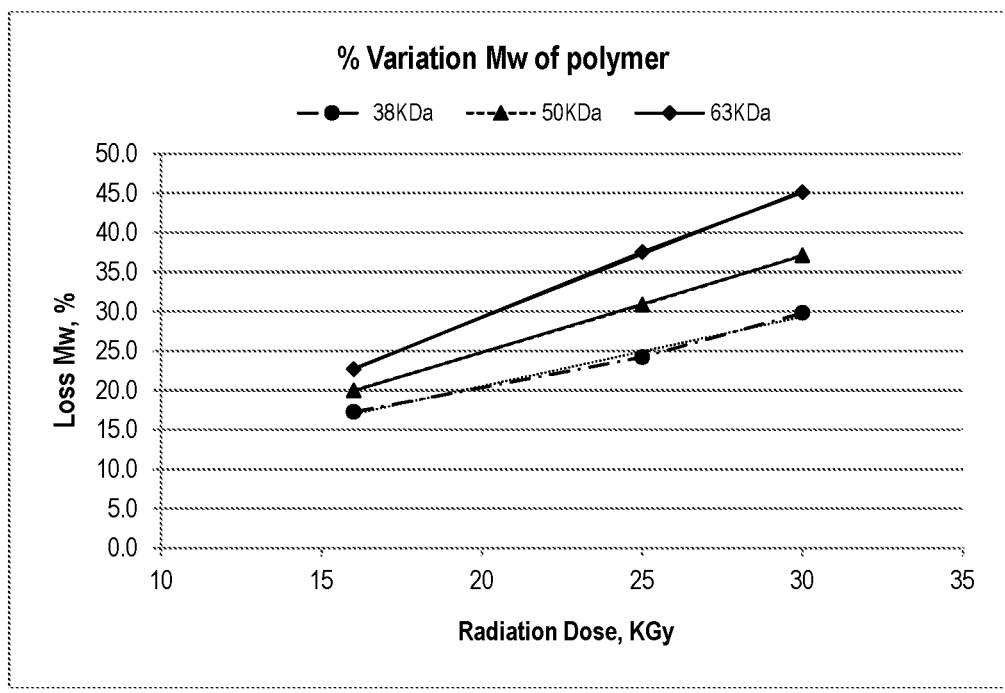
FIG. 11.—Loss of molecular weight percentage in the custom design. The molecular weight of the polymer can be varied by irradiating it with a certain radiation dose. The table describes the percentage of loss of polymer weight versus radiation dose.

A commercial polymer with the required molecular weight can certainly be used. However, we have determined that the essential range of its molecular weight is between 30-46 and preferably between 30-45 kDa. Additionally we have determined in an in-house custom design that the molecular weight of the polymer can be varied by irradiating it with a radiation dose of between 15 and 30 kGy ±10% or even more at a temperature lower than 8° C. and this was not obvious in view of the state of the art to the skilled person (see FIG. 11). For example, the molecular weight of a commercially available polymer in a certain moment can be 50 KDa as an average value. We have determined a method for varying this molecular weight by irradiating the polymer with a certain dose of radiation that can be previously calculated. If done under controlled conditions, it is possible to obtain a mathematical model showing that the molecular weight of the polymer can be decreased with increasing irradiation doses. Since, if the molecular weight of the polymer is adjusted, its inherent viscosity is correspondingly varied, it follows that by irradiating the polymer with certain defined radiation doses we achieve both the adjustment of its molecular weight and its inherent viscosity. For example:

When a PLGA polymer having a molecular weight between 30 and 46 kDa and an inherent viscosity value in the range of 0.25-0.31 dl/g is needed, and we have as the starting polymer a polymer with 56 KDa of average molecular weight, we have determined that a radiation dose of 25 KGy is required to reduce its molecular weight to the cited range of 30-46 kDa.

When a PLGA polymer having a molecular weight between 30 and 40 and preferably between 30 and 36 kDa and an inherent viscosity value in the range of 0.25-0.31 dl/g and preferably 0.26-0.29 dl/g is needed, and we have as the starting polymer a polymer with 50 KDa of average molecular weight, we have determined that a radiation dose of 25 KGy is required to reduce its molecular weight to the cited range of 30-40 kDa and preferably 36-40 kDa.

When a PLGA polymer having a molecular weight between 30 and 40 kDa and an inherent viscosity value in the range of 0.25-0.31 dl/g is needed, and we have as the starting polymer a polymer with 38 KDa of average molecular weight, we have determined that there is no need to use any radiation dose.

When a PLGA polymer having a molecular weight between 30 and 36 kDa and an inherent viscosity value in the range of 0.25-0.31 and preferably of 0.26-0.29 dl/g is needed, and we have as the starting polymer a polymer with 38 KDa of average molecular weight, we have determined that a radiation dose of 16 KGy is required to reduce its molecular weight to the cited range of 30-36 kDa.

When a PLGA polymer having a molecular weight between 30 and 36 kDa and an inherent viscosity value in the range of 0.25-0.31 and preferably of 0.26-0.29 dl/g is needed, and we have as the starting polymer a polymer with 31 KDa of average molecular weight, we have determined that there is no need to use any radiation dose.

When a PLGA polymer having a molecular weight between 30 and 46 kDa and an inherent viscosity value in the range of 0.25-0.31 and preferably of 0.26-0.29 dl/g is needed, and we have as the starting polymer a polymer with 63 KDa of average molecular weight, we have determined that a radiation dose of 30 KGy is required to reduce its molecular weight to the cited range of 30-46 kDa and preferably of 30-36 kDa.

In these experimental tests, the temperature conditions for the polymer during the irradiation were about 8° C. However, other temperatures can be used, such as e.g. lower than 35° C., or lower than 25° C., although in these cases the relationships between the radiation dose and the resulting molecular weight may vary.

The irradiation procedure is especially suitable for the manufacturing of the compositions described herein. Furthermore, the filling of the solid polymer into syringes generally represents a real challenge in the manufacturing of injectable formulations. The polymer, manufactured as a non-sterile product, requires sterilization in order to be suitable for injection. We subjected the polymer to sterilization by gamma- or beta-irradiation. Irradiation represents a challenging issue when using biodegradable polymers, as irradiation can disrupt the chains into fractions of smaller size. Control of the polymer molecular weight appears as again as the critical parameter to control the final characteristics of a product after a sterilization process.

Chain size reduction by irradiation can be mathematically modelled or controlled in order to predict the final molecular weight of a polymer to be used as raw material having a molecular weight higher than desired. Therefore, once determined the fill weight of the polymer to be filled in a container (for example, the fill weight of the polymer in a syringe) and the bio-burden present in the polymer as raw material, the irradiation dose required to get the polymer sterile (as specified by ISO 11137) is selected for the required fill weight. Then the mathematical model describing the loss of molecular weight for a certain polymer versus the irradiated dose can identify the initial molecular weight of the polymer to be used as raw material required obtaining, after the irradiation process, a polymer with the desired final molecular weight for the formulation. As the availability of a polymer with a specific molecular weight can be somewhat limited, then we can alternatively select an available polymer with a molecular weight that is higher to what is required according to the irradiation dose identified, and then adjust the irradiation dose to a higher value in order to obtain a sterile polymer with the required molecular weight.

The concentration of the polymeric component in the compositions of the invention is in the range of 24%-50% wt, 24%-40% wt, 24%-30% wt, 25-27% wt or 26% wt, (expressed as the percentage of polymer weight based on total composition weight).

The preferred solvents are non-toxic, biocompatible and appropriate for parenteral injection. Solvents susceptible of causing toxicity should not be used for the injection of any material into any living body. More preferably, selected solvents are biocompatible in order not to cause any severe tissue irritation or necrosis at the injection site. Therefore, the solvent is preferably classified as class II or III, and more preferably class III, according to ICH Guidelines. For the formation of the in-situ implant, the solvent should preferably diffuse quickly from the polymeric solution towards surrounding tissues when is exposed to physiological fluids. Consequently, the solvent is preferably DMSO.

The drug is preferably risperidone, and/or paliperidone and all pharmaceutically acceptable salts or combinations thereof. This drug is preferably at least partly suspended in the solvent. The solubility of the drug in the solvent is preferably lower than 90 mg/ml, more preferably lower than 65 mg/ml, and most preferably below 10 mg/ml. The advantage of this low solubility is that the initial burst of the drug when the solvent diffuses to the external aqueous medium is greatly reduced. In addition, in the final compositions of the invention the drug is provided in a concentration (the drug content) between 4 and 16 wt %, expressed as the percentage of the drug with respect to the total composition weight (drug+polymer+solvent). In some embodiments, the drug content ranges from about 4% to about 16% wt, about 7% to about 15% wt, about 10% to about 15% wt, about 12% to about 14% wt, or about 13% wt After administration, the injectable composition forms an implant that provides a satisfactorily controlled release profile for the drug. By "satisfactorily controlled" release profile is meant that the implant will exhibit an initial release profile that is not too steep (fast), which would otherwise lead to plasma levels that are too high with concomitant toxic side effects, and an initial release profile that is not too flat (slow), which would lead to plasma levels that are below therapeutic concentrations. An implant exhibiting a satisfactorily controlled initial release profile will release will release no more than 20% wt., no more than 15% wt, no more than 12% wt, no more than 10% wt, no more than 8% wt no more than 6% wt, no more than 5% wt, no more than 4% wt, no more than 3% wt, no more than 2% wt or no more than 1% wt of its charge of drug within 24 hours after being placed in an aqueous environment. It will release at least 0.1% wt, at least 0.5% wt., at least 1% wt, at least 2% wt., at least 3% wt or at least 4% wt of its charge of drug within 24 hours after being placed in an aqueous environment. The invention includes all combinations of the embodiments herein.

One of the factors contributing to control the initial release of the composition of the invention is the viscosity of the polymeric solution. In some embodiments, at least 80%, at least 90%, at least 95%, at least 99% or all of the polymer is dissolved in the solvent. If not otherwise specified, the viscosity value of the polymeric solution or the injectable composition is given in Pa·s units, measured in chloroform at 25° C. and at concentration of 0.1% wt/v. The "polymeric solution", which is defined as the combination of the polymer and the solvent where it is dissolved, has a preferred viscosity in the range of 1.5-2.1±10% Pa·s, in the range of 1.6-1.9±10% Pa·s or in the range of 1.7-1.8±10% Pa·s. The viscosity can be controlled primarily according to the molecular weight (the intrinsic or inherent viscosity) of the polymer and the concentration of polymer in the injectable composition.

Another factor contributing to control the initial release of the compositions of the invention is the biocompatible copolymer molecular weight that must be between 30 and 46 and preferably between 30 and 45 kDa. The adequate balance in this composition between drug solubility in the solvent and the molecular weight of the polymer in the implant (that controls the polymer precipitation process and the final structural characteristics of the implant) allows the formulation to limit the amount of risperidone that can be released in the solvent diffusion phase after the intramuscular injection. Once the formulation is injected in the intramuscular tissue, the DMSO is rapidly dissolved in the surrounding aqueous environment. The relative increase of the polymer concentration in DMSO over the polymer solubility in the solvent leads to the formation of a polymer precipitate that entraps the risperidone that was not solubilized in the solvent. Molecular weight of the polymer has an impact upon this critical step, as PLGA chains with too low a molecular weight exhibit delayed precipitation time compared to the chains possessing a molecular weight in the required range. This delayed precipitation allows the drug to increase contact with the surrounding fluids and increases the initial amount or rate of drug release. Therefore, low molecular weighed chains lead to an excessive release of risperidone after the injection and potentially lead to toxic plasma levels on the first days after the injection. Molecular weight of the polymer also can affect the release of the drug from the intramuscularly injected implant after solvent diffusion and polymer precipitation. Molecular weights over the specified range are not capable of maintaining adequate release rates of risperidone or paliperidone by diffusion. Additionally, higher molecular weight chains in the intramuscular tissue require longer hydrolysis times in order to provide soluble fractions that could release the drug entrapped in the polymer matrix. The increased amount of unreleased drug remaining in an implant at the end of a dosing period, e.g. at the end of 28-35 days, might lead to undesirably high active moiety plasma concentrations, or plasma concentrations after 30 days post injection that could somehow interfere with subsequent doses, given that the formulation is generally intended for sequential administration every 4 weeks to 30 days.

The invention provides an injectable intramuscular depot composition suitable for forming an in situ solid implant in a body, the composition comprising: a drug which is risperidone and/or paliperidone or any pharmaceutically acceptable salt thereof in any combination; a biocompatible PLGA copolymer based on lactic and glycolic acid and having a monomer ratio of lactic to glycolic acid of ranging from 45:55 to 55:45 and preferably about 50:50, i.e. 50:50±10%; and DMSO, wherein the composition releases the drug with an immediate onset of action and continuously for at least 4 weeks, and wherein the composition has a pharmacokinetic profile in vivo that makes it suitable for administration every about 4 weeks or even longer periods characterised in that the biocompatible copolymer has a molecular weight between 30 and 46 kDa, preferably between 30 and 36 kDa, and has an inherent viscosity in the range of 0.25-0.31 ±10% dl/g or 0.26-0.29±10% dl/g.

In a preferred embodiment of the invention, the biocompatible copolymer is gamma- or beta-irradiated in the dose range of 15-30 KGy and at a temperature higher than -40° C. but lower than 35° C., more preferably lower than 25° C., even more preferably lower than 15° C. and most preferably about 8° C., for adjusting its molecular weight and viscosity ranges.

Yet another factor that may contribute toward controlling the initial release of drug from the implant is the drug's particle size. Large particles provide a smaller surface area per weight thereby reducing the initial release (burst) but the release may be then delayed until the beginning of the degradation of the polymeric matrix. On the other hand, small particles evoke higher burst levels due to increased surface area and easier drug diffusion from small particles during implant hardening, followed by continuous drug release levels due to the combination of the processes of drug diffusion and implant erosion. Consequently, in a preferred embodiment of the invention a wide particle size distribution, combining large and small particle sizes in different ratios, is used in order to reduce the initial burst and still maintain a suitable constant drug release by diffusion of smaller particles during the first phase of release and gradual release of drug from the bigger particles while the polymer degrades, i.e. during the period of time (days to weeks) following the initial burst phase.

If not otherwise specified, the particle size distribution was determined by light scattering technique using laser light diffraction in wet mode. It is known that particle size distribution results can be altered as a function of the material treatment such the use of high concentrate surfactant agents and/or strong force energies (vortex, sonication, etc). If nothing else is mentioned, drug is not treated and samples are prepared by direct addition to the tank under moderate stirring (2000-3500 rpm). The methodology applied on present invention to determine the drug particle size distribution mimics in a more faithfully way the behavior of the drug powder on the injectable formulation herein described than other methods which apply force energies to the sample and/or use high concentrate surfactant agents for preparing the samples in order to achieve high degrees of powder disaggregation that cannot be simulated during the manual reconstitution process of the formulation.

In some embodiments, the particle size distribution of the drug is as follows: not more than 10% of the total volume of drug particles are less than 10 microns in size (equivalent diameter in volume as a function of applying Fraunhofer theory to irregularly shape particles; as measured by laser light scattering, such as with a Malvern Mastersizer 2000) and not more than 10% of the total volume of drug particles are greater than 225 microns in size. In addition, the drug particles possess a d0.5 value preferably in the range of about 60-130 microns.

In some embodiments, the drug exhibits one of the following particle size distributions:

| Parameter | I | II | III | IV | V | VI |
|---|---|---|---|---|---|---|
| d0.1 (microns) | 27.49 | <30 | 17.41 | ≤20 | ≤10 | ≤10 |
| d0.5 (microns) | 79.90 | 40-130 | 51.61 | 40-130 | 40-130 | 40-130 |
| d0.9 (microns) | 176.66 | >170 | 175.32 | >170 | >225 | >200 |

In a preferred embodiment of the invention, this drug has the particle size distribution as follows:
less than 10% particles smaller than 10 microns;
less than 10% particles larger than 225 microns, and a d0.5 value in the range of 40-130 microns.

Additional parameters such as the mass ratio of drug to polymeric solution (polymer+solvent), the mass ratio of drug to (polymer+drug), the mass ratio of solvent/drug, the mass ratio of polymer to polymeric solution (polymer+solvent), the mass ratio of solvent to polymeric solution (polymer+solvent), can also be useful to provide control over the initial release and/or controlled release of drug from the compositions of the invention.

In some embodiments, the mass ratio of polymeric solution to drug, expressed as the mass of (polymer+solvent) to the mass drug, ranges from about 15:1 to about 5:1, about 12:1 to about 5:1, from about 7:1 to about 6.5:1, about 6.5:1 to about 6.8:1, about 6.67:1 or about 6.68:1.

In some embodiments, the mass ratio of drug to (polymer+drug), expressed as the percentage of the drug weight with respect to total weight of the drug plus polymer, is in the range of about 15-40% weight, about 25-35% wt, about 30-35%, about 31-35%, about 32-34% or about 33% wt.

In some embodiments, the mass ratio of solvent to drug is in the range of about 12:1 to about 4:1, about 10:1 to about 4:1, about 5:1 to about 4:1, about 4.6:1 to about 4.7:1, about 4.67:1, about 4.66:1 or about 4.68:1.

In some embodiments, the mass ratio of polymer to polymeric solution, expressed as the weight percentage of polymer with respect to the weight of polymer+solvent, is about 25-50%, about 25-35%, about 30-40%, about 28-32%, or about 30%.

In some embodiments, the mass ratio of solvent to polymeric solution, expressed as the weight percentage of solvent with respect to the weight of polymer+solvent, is about 60-80%, about 65-75%, about 67-72%, or about 70%.

In some embodiments, the drug/polymer+drug mass ratio is about 33%, the content of drug is about 13% w/w of total formulation, the viscosity of the polymeric solution (PLGA polymer and DMSO) is in the range of about 1.5-2.1±10% P·a·s or about 1.7-1.8±10% P·a·s.

In some embodiments, the drug is partially suspended with a solubility of drug in the DMSO solvent below 10 mg/ml. In some embodiments, the drug is partially dissolved or substantially completely undissolved in the solvent, DMSO, polymeric solution or injectable composition. In some embodiments, 2.5%, 5%, 7.5%, 10%, 20% or <25%, of the drug is dissolved in the solvent or polymeric solution to form the injectable composition. In some embodiments, >0%, 4.5%, 1%, 5%, 10% or 15% or up to about 20% wt. of the drug is dissolved in the solvent or polymeric solution to form the injectable composition. All combinations of these embodiments are contemplated.

According another embodiment, the biocompatible copolymer of this invention is gamma- or beta-radiated, preferably in the range of 10-30 KGy, more preferably in the range of 15-30 KGy, and most preferably between 16-25 KGy±10%.

According to another embodiment, the composition is a sterile composition and is suitable for the treatment of schizophrenia or bipolar disorders in the human body.

Another aspect of the invention provides a method for the treatment of a disease, disorder or condition that is therapeutically responsive to a risperidone and/or paliperidone, the method comprising administering an amount of injectable composition, as defined herein, to a subject in need thereof, wherein the amount of injectable composition comprises a dose of drug and the injectable composition continuously provides therapeutically effective plasma levels of drug in the subject throughout a dosing period of at least four weeks beginning from the day of administration.

The injectable composition can also be used to treat a psychotic disease or disorder selected from the group consisting of delusional psychosis, psychotic depression, obsessive-compulsion disorder, schizophrenia, bipolar disorder, schizoaffective disorders, non-schizophrenic psychoses, Asperger's syndrome, Tourette's syndrome, obsessive-compulsion disorder, post-traumatic stress disorder, attention deficit hyperactivity disorder, personality disorders, aggression, depression, dementia, intellectual disabilities and behavioral disturbances in mental retardation and autism, autistic spectrum disorders, anxiety, eating disorders, nervous anxiety, insomnia, idiopathic dystonia, substance abuse, and any combination thereof. The injectable composition can also be used as an antihistaminic for the treatment of allergic disorders or as a prolactin secretion promoter for breastfeeding women or for the treatment of prolactin deficiency.

Figure 9:
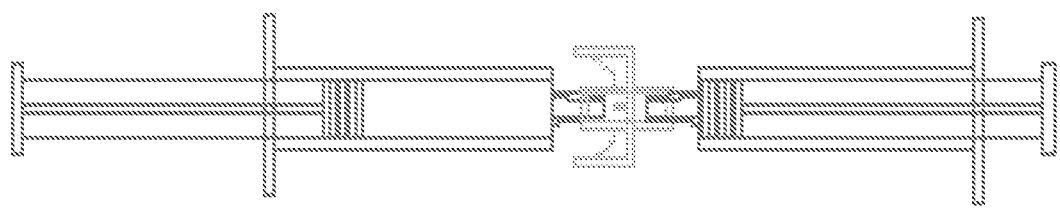
FIG. 9.—Drawing of a kit suitable for the preparation of risperidone and paliperidone compositions comprising two male syringes linked by a connector. Polymer+risperidone are contained in one syringe and DMSO filled in the second syringe FIG. 10.—Drawing of a kit suitable for the preparation of risperidone and paliperidone compositions comprising a female syringe linked to a male syringe. Polymer+risperidone can be contained in one syringe and DMSO filled in the second syringe. Preferably female syringe contains polymer risperidone as a solids and male syringe is filled with DMSO.
Figure 10:

In yet another embodiment, the invention provides a pharmaceutical kit suitable for the in situ formation of a biodegradable implant in a body comprising the composition claimed, wherein the drug and the biocompatible polymer are contained in a first container, and the solvent is contained in a second, separate container. Preferably, at least one of the first and second containers is a syringe, a vial, a device or a cartridge, either disposable or not and more preferably both the first and the second containers are disposable syringes. This aspect of the invention is directed to a kit comprising a first container, preferably syringes, vials, devices or cartridges, all of them either being disposable or not, containing a polymer in solid form, such as PLGA and a drug in the appropriate amounts and a second container, likewise preferably syringes, vials, devices or cartridges, all of them being either disposable or not, containing the water-miscible solvent. When required, the contents of both containers are combined, for example through a connector or by using male-female syringes, and mixed each other so that the compositions according to the invention are reconstituted, for example by moving forwards and backwards the plungers of the syringes. Illustrative preferred embodiments are shown in FIG. 9 (syringes connected through a connector device) and in FIG. 10 (syringes connected through a direct thread).

According to another aspect, the invention provides a method for manufacturing an injectable composition, the method comprising: providing a biocompatible copolymer having a polymer weight higher than required for the intramuscular depot composition; and then reducing its molecular weight to between 30 and 46 kDa by irradiating it with gamma or beta radiation in the dose range of 15-30KGy.

In some embodiments, when the biocompatible polymer has an initial molecular weight of about 56 kDa, it is irradiated with a radiation dose of about 25 KGy to reduce its molecular weight to between 30 and 46 kDa±10%.

In some embodiments, when the biocompatible polymer has an initial molecular weight of about 50 kDa, it is irradiated with a radiation dose of about 25 KGy to reduce its molecular weight to between 30 and 40 and preferably between 30 and 36 kDa±10%.

In some embodiments, when the biocompatible polymer has an initial molecular weight of about 38 kDa, it is irradiated with a radiation dose of about 16 KGy to reduce its molecular weight to between 30 and 36 kDa.

In some embodiments, when the biocompatible polymer has an initial molecular weight of about 63 kDa, it is irradiated with a radiation dose of about 30 KGy to reduce its molecular weight to between 30 and 46 and preferably between 30 and 36 kDa±10%.

According another aspect, the invention provides a dosing regimen method for administering the injectable intramuscular depot composition to a patient in need of psychiatric treatment comprising:
  a) administering intramuscularly to the patient a first dose in the amount of 37 mg to 150 mg of the injectable depot composition;
  b) then administering a subsequent dose of the injectable depot composition in the amount of 37 mg to 150 mg, at a point of time between the 24$^{th}$ day and the 35$^{th}$ day counting from the previous administration day; and
  c) repeating step b) as many times whenever required.

Preferably, the first dose is about 50 mg to about 100 mg and this is equivalent to other subsequent doses.

Within a treatment period, administered doses of injectable composition can be the same or different. In some embodiments, a prior dose is higher or lower than a following dose in a sequence of doses. Two or more doses administered in a treatment period can be the same or different. In some embodiments, two or more doses administered in a treatment period are the same. In some embodiments, two or more doses administered in a treatment period are different. Combinations of these embodiments are within the scope of the invention.

In a preferred embodiment, the injectable depot composition is sterile as a finished product. In other preferred embodiment, the biocompatible polymer is sterilized previously to its aseptic filling process, preferably by irradiation in the range 15-30KGy or by other process like filtration.

All values disclosed herein may have standard technical measure error (standard deviation) of ±10%.

Although not required, the present injectable composition can further comprise an alkaline agent. An alkaline agent with low water solubility such as lower than 0.02 mg/ml can be included. The alkaline agent can be present in a molar ratio >2/5 (drug/alkaline agent), meaning that the alkaline agent is present in molar excess over the drug. Preferred alkaline agents are alkaline or alkaline-earth hydroxides, such as magnesium hydroxide or aluminum hydroxide. Due to the limited water solubility of the alkaline agent, the d 0,5 of the particle size distribution, e.g. of the magnesium hydroxide, is preferably below 10 microns.

It may be necessary to use a starting dosing regimen in order to accelerate obtaining the desired plasma levels before starting the 4 weekly dosing regimen. This starting regimen could be, for example but not limited to, as is described below:
  A first intramuscular dose of the formulation at day 0, in a dose between 25 to 200 mg, followed by a second dose between days 5-10 with a dose in the range of 25 to 200 mg, followed by a third dose between days 28-35 after the first dose, with a dose in the range of 25-200 mg, and then subsequent 4 weekly doses of the formulation;
  A first intramuscular dose of the formulation at day 0, in a dose between 75 to 200 mg, followed by a second dose between days 28-35 with a dose in the range of 25 to 200 mg, and then subsequent 4 weekly doses of the formulation; or
  Any other combination of strengths and intervals needed to obtain the plasma levels needed to start a 4 weekly administration.

The intramuscular dose can be administered to any muscle or muscle group typically recognized by the pharmaceutical industry as a suitable site for an injectable composition. In some embodiments, the composition is administered to the gluteal and/or deltoid muscles. The composition can also be administered to the quadriceps muscle group.

Administration of a single dose is typically considered that amount of injectable composition administered to a subject within a period of up to 24 hours, up to 12 hours, up to 6 hours, up to 3 hours, up to one hour, up to 30 min, up to 15 min or up to 5 min.

A dose of injectable composition refers to an amount of injectable composition comprising a specified dose of drug. Accordingly, a dose of 25-200 mg of injectable composition comprises a dose of 25-200 mg of drug; therefore, the actual amount of injectable composition administered would be greater than 25-200 mg, the actual amount of injectable composition being determined according to the content drug in the injectable composition.

A dose can be administered to a single muscular site or can be divided into two or more portions and administered to two or more muscular sites of a subject. For example, a first portion of a dose can be administered to a first section of gluteal muscle and a second portion of the dose can be administered to a second section of gluteal muscle of a subject.

As used herein, the term "dosing period" refers to the period of days or weeks as measured from the initial day after administration of a dose to at least 28 days after administration or to administration of a subsequent dose. During the dosing period, the implant will provide therapeutic plasma levels of drug for at least at least 4-5 weeks. A dosing period can end after expiration of a predetermined number of days or after the plasma level of drug drops below therapeutic levels.

As used herein, a "treatment period" refers to the weeks, months or years during which implants of the invention are administered to a subject. A treatment period generally comprises plural dosing periods. Dosing periods can occur sequentially or in an overlapping manner during a treatment period. For example, a first dose of injectable composition is administered and a second dose of injectable composition can be administered at a time following administration of the first dose, such that each dose will have its own corresponding dosing period, and the dosing periods would overlapµDosing periods will typically be sequential or overlap by no more than one or seven days.

The injectable composition can be administered to a subject in one or more injection sites on the same day and still be considered as being part of the same dosing period. For example, part of a dose can be administered to a first injection site and another part of the same dose can be administered to another injection site. A single-body implant will form at each injection site. Such a mode of administration within a same day is considered to be administration of a single dose with a single dosing period.

Alternatively, administration can be modified such that there is one point of needle entry into the subject but more than one injection site below the skin, which can be achieved by making a first penetration into the skin and muscle and administering a portion of a dose, then partially withdrawing and redirecting the needle into another section of muscle, while maintaining the tip of the needle beneath the skin, and then injecting another portion of the dose into this other section of muscle. Such a mode of administration is still considered to be administration of a single dose within a single dosing period.

The plasma concentration profile during the dosing period can exhibit one, two, or more maxima and one, two or more minima. An initial maximum can be caused by dissolution of drug during the initial day(s) of the dosing period followed by a slowing of the release thereof and another maximum can be caused by increased rate of release during the remaining days of the dosing period. Embodiments of the invention include those wherein: a) the plasma profile exhibits a maximum during the initial one to six days or one to three days of the dosing period; b) the plasma profile exhibits a maximum during the latter 14 to 24 days of a 4-week dosing period; c) the plasma profile exhibits a maximum during the initial days of the dosing period and a maximum during the remaining days of the dosing period; d) the plasma profile is substantially level (a standard deviation within ±30%, ±25%, ±20%, ±15%, ±10% or ±5% of the average or mean) during the dosing period; e) the plasma profile exhibits a maximum during the initial two to six days or two to twelve days of the dosing period; and/or f) the plasma profile exhibits a maximum during the latter 14 to 28 days of a 4- to 5-week dosing period.

The implant of the invention can provide substantially improved plasma levels of drug when compared to another injectable formulation (not according to the invention) containing the same drug when administered on an equivalent dose basis.

As used herein the term, "initial burst" or "initial release" refers to the addition of the plasma levels of drug plus those of active metabolite, which addition is also called "the active moiety" throughout the present specification, from the moment of injection/administration of the injectable composition to a subject in need thereof until completion of the third day after the administration. For example, the drug can be risperidone and its metabolite can be paliperidone. In some embodiments, the initial period of release is within three days, within two days, within one day or within twelve hours after administration.

The injectable depot composition of the invention provides an adequate plasma level profile for drug after administration during a dosing period. An "adequate plasma level profile" is considered as providing not more than (NMT) 45% of the AUC of the paliperidone occurring between the moment of the injection until completion of 30% of a dosing period, between 35% and 45% of the AUC of the paliperidone occurring during the period of time that is after 30% and up to 70% of a dosing period, and not more than 35% of the AUC of the paliperidone occurring during the period of time that is after 70% of a dosing period. The total AUC is determined as the AUC for the entire dosing period.

For an 4-week to 5-week dosing period, an "adequate plasma level profile" is considered as not more than (NMT) 45% of the AUC of the paliperidone occurring between the moment of the injection until day 7 (included), between 35% and 45% of the AUC of the paliperidone occurring between day 7 and day 21 (included), and not more than 35% of the AUC of the paliperidone occurring after day 21 until completion of the dosing period. In some embodiments, the injectable depot composition provides a plasma level profile for drug as follows.

| Formulation | Percentage of Drug AUC During the Period Following Administration (day) | | |
| --- | --- | --- | --- |
| | Day-0 up to day 7 | From day 8 to day 21 | From Day 22 up to day 28 |
| X | NMT 45% of AUC | 35%-45% of AUC | NMT 35% of AUC |
| Y | 20%-45% of AUC | 35%-45% of AUC | 10%-35% of AUC |
| Z | 30%-45% of AUC | 35%-45% of AUC | 20%-35% of AUC |

The above percentages represent an adequate balance between the different periods in which paliperidone is being released from the implant in order to have a formulation to be injected each 4 to 5 weeks or every about 30 days to provide therapeutic plasma levels of paliperidone in a human since the first day of the injection and to provide the desired average paliperidone plasma concentrations during the period between injections and with reduced peak-valley plasma values of paliperidone that could lead to toxicity or lack of efficacy.

The term "about" is intended to mean±10%, ±5%, ±2.5% or ±1% relative to a specified value, i.e. "about" 20% means 20±2%, 20±1%, 20±0.5% or 20±0.25%.

EXAMPLES

The following examples illustrate the invention and should not be considered in a limitative sense thereof.

Acceptable plasma levels of active moiety during the initial burst phase are below 75 ng/ml in Beagle dogs when doses administered are 2.5 mg/kg risperidone.

Example 1

Depot Formulation With Resomer® 503 Without Radiation

In the present example, the following formulation was prepared:

| | Ingredient | Amount (mg) |
| --- | --- | --- |
| Female 2.25 ml syringe | Lactic-co-glycolic acid copolymer (N-capped) with 50% content of each of the two organic acid monomers and a molecular weight of 32 KDa. | 50 |
| Male 2.25 ml syringe | Risperidone | 25 |
| | Dimethyl sulfoxide | 117 |

Risperidone particle size was characterized by light scattering and provided the following distribution of particle size: d(0,1)=27.49 µm, d(0,5)=79.90 µm and d(0,9)=176.66 µm.

Polymer has been characterized for its molecular weight according to the following technique:
Equipment
GPC Chromatograph With Triple Detector (Laser Diffraction, Viscosimetry, Refraction Index)
    Viscotek® GPCmax VE 2001 GPC SOLVENT/SAMPLE MODULE
    Viscotek® TDA 305 TRIPLE DETECTOR ARRAY
Reagents:
    Tetrahydrofurane (THF) grade GPC stabilized with butyl hydroxyl toluene (BHT) 250 ppm
    Polystyrene narrow standard (preferably about a molecular weight of 90 or 99 KDa)

Sample Preparation:
 1-2 mg/ml Standard Sample
 10 mg/ml Test sample: 3 samples for each polymer to be tested
Pre-Conditioning:
 Condition and stabilize column and detectors with mobile phase (THF) until reaching working flow rate of 1 ml/min and purge viscometer and refraction index detectors, checking at the end that all signals are stable and adequate.
Chromatographic conditions:
 Column: 2 serial columns i-MBMMW-3078 (CLM1012, Viscotek)
 Delay column: medium delay (CLM9002, Viscotek)
 Column temperature 30° C.
 Flux rate 1 ml/min
 Injection volume: 100 µl
 Run time: 35 minutes
 Eluent: stabilized THF (pre-heated to 30° C. and under 100 rpm agitation)
System verification: Inject 100 µl of eluent and check there is no response in signals related with molecular weight determination
 Inject 100 µl of polystyrene narrow standard and check adequacy of the measurement. Repeat at least twice.
 Acceptance Criteria: ±5% of the nominal Molecular Weight and ±3% Intrinsic Viscosity declared by manufacturer standard certificate.
Calibration:
 Not necessary if system verification complies and no previous chromatographic conditions are changed.
 In case it would be required to calibrate:
 Inject 100 µl of polystyrene standard at least twice.
 Use first sample's data for triple calibration by creating a new multidetectors—homopolymer's method.
 Introduce into the method all the data needed for internal calibration such standard values of MW, IV, dn/dc, dA/dc and refractive index of the solvent.
 Calibrate the system as the equipment specify and save the new method.
 Check with the new method the adequacy of the measurement for the second injection of the standard.
Procedure:
 Inject by triplicate 100 µl of the test sample
 Polymer molecular weight measured according to the technique specified resulted in 32 KDa. According to a similar technique, inherent viscosity of the polymer resulted in a value of 0.27 dl/g. It is important to mention that inherent viscosity values correspond to those obtained with the technique described, specially related to temperature conditions and eluent used. Any change in measurement conditions mean the obtention of different values as directly depend on them.
 The risperidone implantable formulation was prepared by connecting male and female syringes and moving the plungers forwards and backwards upon complete dissolution of the polymer and the formation of a homogeneous suspension of the risperidone in the polymer dissolution.
In Vivo Plasma Levels After Intramuscular Administration to Beadle Dog:
 The risperidone composition of this example was intramuscularly injected to Beagle dogs weighing an average of 10 kg. The amount injected corresponded to a dose of 25 mg risperidone and the composition was intramuscularly placed in the left hind leg using a syringe with a 20 G needle. Total number of dogs was 3. After injection, plasma levels were obtained at 0, 4 h, 1 d, 2 d, 3 d, 5 d, 7 d, 10 d, 15 d, 17 d, 21 d, 24 d, 28 d, 30 d, 35 d, 37 d and 42 d.

The kinetics of the plasma levels corresponding to the risperidone active moiety was evaluated by measuring both risperidone and its active metabolite 9-OH-risperidone in the plasma samples. The profile of the plasma levels of the risperidone active moiety and the AUC values calculated are shown in FIG. 1. The results are expressed as the addition of risperidone plus 9-OH-risperidone concentrations (ng/ml) as the function of time, since the therapeutic activity of 9-OH-risperidone is substantially equivalent to that of risperidone.

As it can be observed in this Figure, the injection of an amount of composition equivalent to 25 mg risperidone to Beagle dogs resulted in very high control of the initial burst release followed by a slow, sustained decrease, with continuous plasma levels from day 1 onwards.

The plasma levels profile for the active moiety, as previously described, can be considered adequate as provide very low risk of having toxic plasma levels just after the injection. The adequate balance in this composition between drug solubility in the solvent and the molecular weight of the polymer in the implant (that controls the polymer precipitation process and the final structural characteristics of the implant) allows the formulation to limit the amount of risperidone that can be released in the solvent diffusion phase after the intramuscular injection.

Once the formulation is injected in the intramuscular tissue, the DMSO is rapidly dissolved in the surrounding aqueous environment. The relative increase of the polymer concentration in DMSO over the polymer solubility in the solvent leads to the formation of a polymer precipitate that entraps the risperidone that was not solubilized in the solvent. Molecular weight of the polymer has a great impact in this critical step, as too low weighed chains have delayed precipitation time compared to the chains having the weight in the adequate range. This delayed precipitation allows the drug to increase contact with the surrounding fluids towards the drug is being released. Therefore, low molecular weighed chains lead to an excessive release of risperidone after the injection and potentially to obtain toxic plasma levels on the first days after the injection. Molecular weight of the polymer also can affect the release of the drug from the intramuscularly injected implant after solvent diffusion and polymer precipitation.

Molecular weights over the specified range are not capable to maintain adequate release rates of risperidone by diffusion. Additionally, higher molecular weight chains in the intramuscular tissue require longer hydrolysis times in order to provide soluble fractions that could release the drug entrapped in the polymer matrix. A higher remaining drug content to be released could lead to the obtention of undesirably high active moiety plasma values, or plasma values after 30 days post injection that could somehow interfere with the following dose as the formulation is intended to be injected several times into the human, each 4 weeks or 30 days.

The FIG. 1 shows how a polymer in the 30-36 KDa region (32KDa) is capable to provide desirable in vivo plasma levels profile.

| | AUC all (h * ng/ml) | $AUC_{0-7}$ days (h * ng/ml) | $AUC_{7-21}$ days (h * ng/ml) | $AUC_{21-last}$ (h * ng/ml) |
|---|---|---|---|---|
| Dose 2.5 mg/kg | 20259.70 | 7039.78 | 8657.52 | 4562.40 |

Example 2

Depot Formulation With Resomer® 504 Radiated to 16 KGy

The present example shows how the polymer molecular weight can be controlled in order to have a sterile formulation with the desired in vivo release properties.

Filling solid polymer in syringes represents a real challenge in the manufacturing of injectable formulations. The polymer, manufactured as a non-sterile product, requires undergoing sterilization in order to achieve a formulation that can be injected into human beings. Probably the best way to solve this technical issue is to subject the polymer to sterilization by gamma or beta irradiation. Irradiation represents a challenging issue when used biodegradable polymers, as irradiation can disrupt the chains into fractions of smaller size. Control of the polymer molecular weight appears as again as the critical parameter to control the final characteristics of a product after a sterilization process.

However, chain size reduction by irradiation can be mathematically modelled or controlled in order to predict the final molecular weight of a polymer to be used as raw material having a molecular weight higher than desired. Therefore, once determined the fill weight of the polymer to be filled in a container (for example, the fill weight of the polymer in a syringe) and the bio-burden present in the polymer as raw material, the irradiation dose required to get the polymer sterile (as specified by ISO 11137) is selected for the required fill weight.

Then the mathematical model describing the loss of molecular weight for a certain polymer versus the irradiated dose can identify the initial molecular weight of the polymer to be used as raw material required obtaining, after the irradiation process, a polymer with the desired final molecular weight for the formulation.

As the availability of a polymer with a specific molecular weight can be somewhat limited, then we can alternatively select an available polymer with a molecular weight that is higher to what is required according to the irradiation dose identified, and then adjust the irradiation dose to a higher value in order to obtain a sterile polymer with the required molecular weight. In this example, a lactic-co-glycolic acid copolymer with 50% content of each of the two organic acid monomers and a molecular weight of 38 KDa was sterilized by beta irradiation at 16 KGy under controlled temperature and moisture conditions. The resultant polymer was characterized for its molecular weight according to the method described in example 1. Molecular weight after irradiation process was 31 KDa.

| | Ingredient | Amount (mg) |
|---|---|---|
| Female 2.25 ml syringe | Lactic-co-glycolic acid copolymer (N-capped) with 50% content of each of the two organic acid monomers and a molecular weight of 38 KDa, beta-irradiated as a bulk with a 16 KGy dose achieving a final molecular weight of 31 KDa. | 50 |
| | Risperidone | 25 |
| Male 2.25 ml syringe | Dimethyl sulfoxide | 117 |

Risperidone particle size was characterized by light scattering and provided the following distribution of particle size: d(0,1)=27.49 μm, d(0,5)=79.90 μm and d(0,9)=176.66 μm.

Inherent viscosity of the irradiated polymer, as calculated by the technique described in example 1 was 0.27 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

In Vivo Plasma Levels After Intramuscular Administration to Beagle Dog:

The risperidone composition of this example was intramuscularly injected to Beagle dogs weighing an average of 10 kg. Two cohorts were studied at two different doses: 2.5 mg/kg and 5.0 mg/kg. The composition was intramuscularly placed in the left hind leg using a syringe with a 20G needle. Total number of dogs on each cohort was 6. After injection, plasma levels were obtained at 0, 4 h, 1 d, 2 d, 3 d, 5 d, 7 d, 10 d, 14 d, 17 d, 21 d, 24 d, 28 d, 30 d, 32 d, 35 d, 38 d, 42 d, 45 d, 49 d, 52 d.

Figure 2:
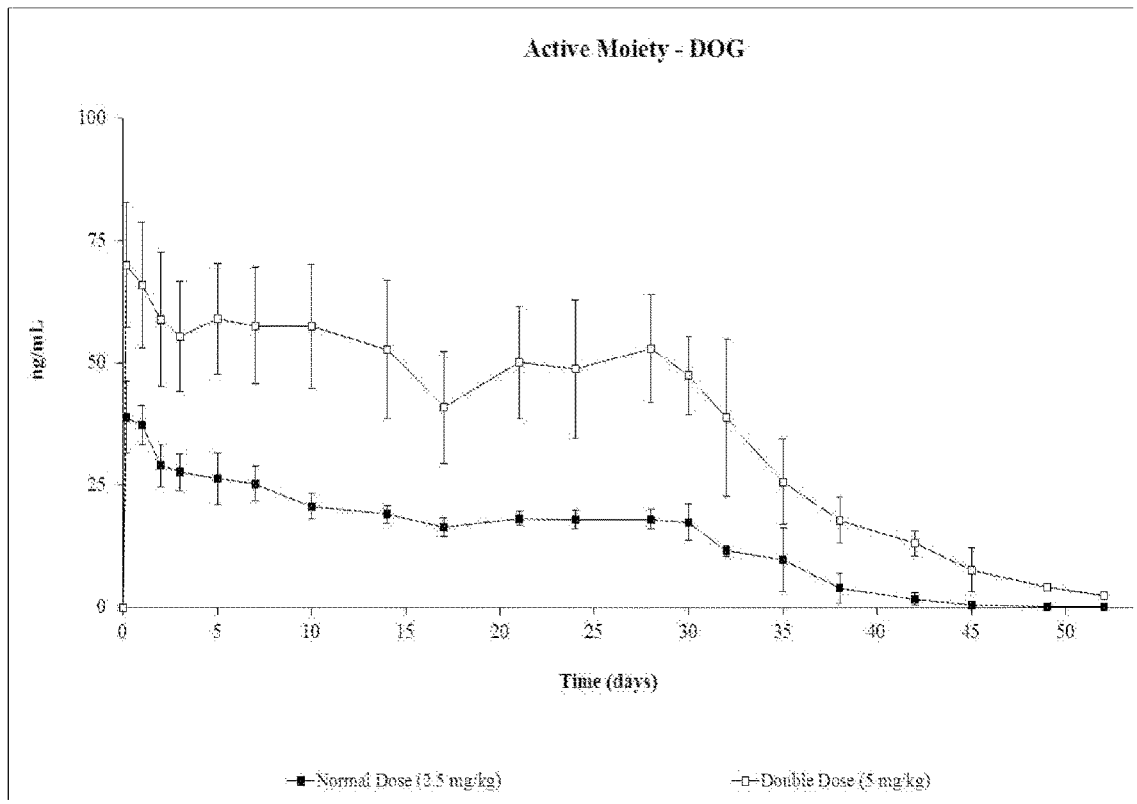
FIG. 2.—Active moiety levels profile in dog after the administration of the risperidone formulation described in example 2 to two cohorts of Beagle dogs (each cohort n=6). Doses were 2.5 and 5 mg/kg. Results are expressed as ng/ml plasma values of active moiety versus time. The table describes Area Under the Curve (AUC) of active moiety plasma levels versus time. AUC all as well as AUC vs three different time frames are included. Units are expressed in h*ng/ml.

The kinetics of the plasma levels corresponding to the risperidone active moiety was evaluated by measuring both risperidone and its active metabolite 9-0H-risperidone in the plasma samples. The profile of the plasma levels of the risperidone active moiety and the AUC values calculated are shown in FIG. 2. The results are expressed as the addition of risperidone plus 9-OH-risperidone concentrations (ng/ml) as the function of time, since the therapeutic activity of 9-0H-risperidone is substantially equivalent to that of risperidone. As it can be observed in this Figure, the injection of an amount of composition equivalent to 2.5 mg/kg and 5.0 mg/kg risperidone to Beagle dogs resulted again in very high control of the initial burst release followed by a slow, sustained decrease, with continuous plasma levels from day 1 onwards.

The FIG. 2 shows how a polymer with higher molecular weight can be adjusted to a desired molecular weight and maintain the release characteristics obtained with a non-irradiated polymer with the original molecular weight in the range of 30-36 KDa, even though small variations in the terminal end groups of the polymer chains can occur after radiation. Again, the plasma levels profile for the active moiety, as previously described, can be considered adequate as provide very low risk of having toxic plasma levels just after the injection.

| | AUC all (h * ng/ml) | $AUC_{0-7}$ days (h * ng/ml) | $AUC_{7-21}$ days (h * ng/ml) | $AUC_{21\text{-}last}$ (h * ng/ml) |
|---|---|---|---|---|
| Dose 2.5 mg/kg | 17537.68 | 4848.4 | 6494.76 | 6194.52 |
| Dose 5 mg/kg | 46924.94 | 9918.74 | 17170.8 | 19835.4 |

Example 3

Depot Formulation With Resomer® 504 Radiated to 25 KGy

This is another example that shows how the polymer molecular weight can be controlled in order to have a sterile formulation with the desired in vivo release properties.

A lactic-co-glycolic acid copolymer with 50% content of each of the two organic acid monomers and a molecular weight of 50 KDa was sterilized by beta irradiation at 25 KGy under controlled temperature and moisture conditions. The resultant polymer was characterized for its molecular weight according to the method described in example 1. Molecular weight after irradiation process was 35 KDa.

| | Ingredient | Amount (mg) |
|---|---|---|
| Female 2.25 ml syringe | Lactic-co-glycolic acid copolymer (N-capped) with 50% content of each of the two organic acid monomers and a molecular weight of 50 KDa, beta-irradiated as a bulk with a 25KGy dose achieving a final molecular weight of 35 KDa. | 50 |
| | Risperidone | 25 |
| Male 2.25 ml syringe | Dimethyl sulfoxide | 117 |

Risperidone particle size was characterized by light scattering and provided the following distribution of particle size: $d(0,1)=27.49$ μm, $d(0,5)=79.90$ μm and $d(0,9)=176.66$ μm.

Inherent viscosity of the irradiated polymer, as calculated by the technique described in example 1 was 0.28 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

In Vivo Plasma Levels After Intramuscular Administration to Beagle Dog:

The risperidone composition of this example was intramuscularly injected to Beagle dogs weighing an average of 10 kg. An amount of formulation equivalent to a dose of 2,5 mg/kg of risperidone was intramuscularly placed in the left hind leg using a syringe with a 20G needle. Total number of dogs was 3 After injection, plasma levels were obtained at 0, 4 h, 1 d, 2 d, 3 d, 5 d, 7 d, 10 d, 14 d, 17 d, 21 d, 24 d, 28 d, 30 d, 32 d, 35 d, 38 d, 42 d, 45 d, 49 d, 52 d.

Figure 3:
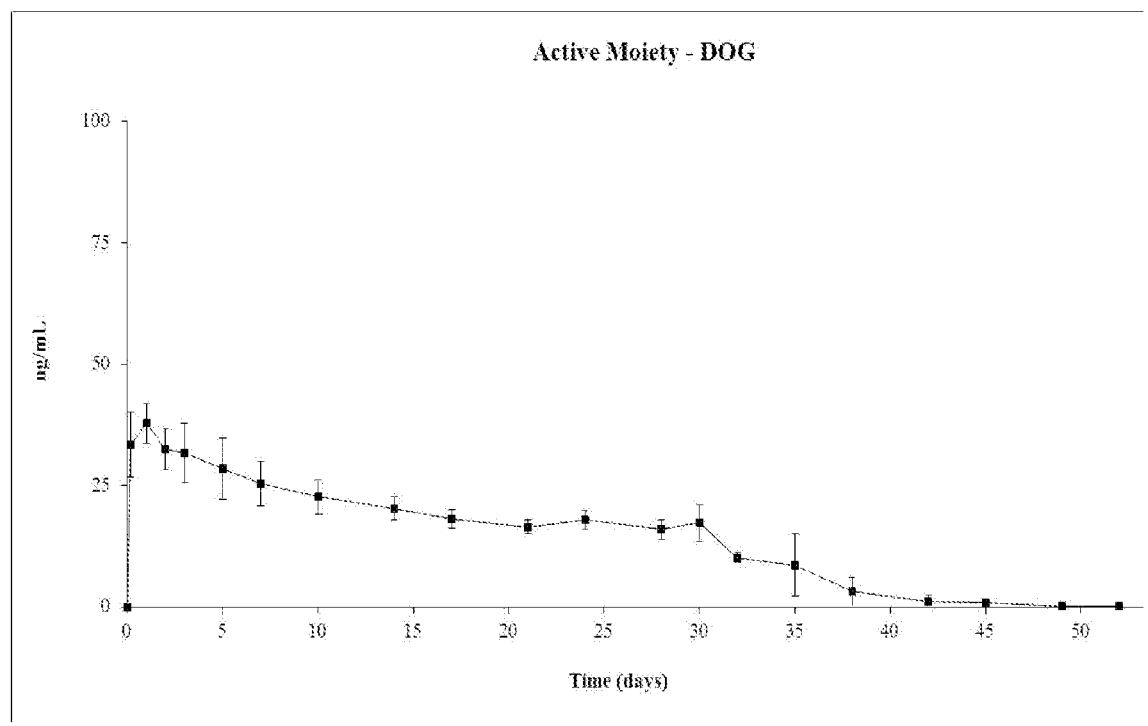
FIG. 3.—Active moiety levels profile in dog after the administration of the risperidone formulation described in example 3 to Beagle dogs (n=3). Dose is 2.5 mg/kg. Results are expressed as ng/ml plasma values of active moiety versus time. The table describes Area Under the Curve (AUC) of active moiety plasma levels versus time. AUC all as well as AUC vs three different time frames are included. Units are expressed in h*ng/ml.

The kinetics of the plasma levels corresponding to the risperidone active moiety was evaluated by measuring both risperidone and its active metabolite 9-OH-risperidone in the plasma samples. The profile of the plasma levels of the risperidone active moiety and the AUC values calculated are shown in FIG. 3. The results are expressed as the addition of risperidone plus 9-OH-risperidone concentrations (ng/ml) as the function of time, since the therapeutic activity of 9-OH-risperidone is substantially equivalent to that of risperidone. As it can be observed in this FIG. 3, the injection of an amount of composition equivalent to 2.5 mg/kg to Beagle dogs resulted again in very high control of the initial burst release followed by a slow, sustained decrease, with continuous plasma levels from day 1 onwards. Once again, the plasma levels profile for the active moiety, as previously described, can be considered adequate as provide very low risk of having toxic plasma levels just after the injection.

| | AUC all (h * ng/ml) | $AUC_{0-7}$ days (h * ng/ml) | $AUC_{7-21}$ days (h * ng/ml) | $AUC_{21\text{-}last}$ (h * ng/ml) |
|---|---|---|---|---|
| Dose 2.5 mg/kg | 17734.84 | 5134 | 6844.08 | 5756.76 |

Example 4

Depot Formulation With Lakeshore Biomaterials® 5050 DLG 5E Radiated to 25 KGy

This is another example that shows how the polymer molecular weight can be controlled in order to have a sterile formulation with the desired in vivo release properties.

A lactic-co-glycolic acid copolymer with 50% content of each of the two organic acid monomers and a molecular weight of 56 KDa was sterilized by beta irradiation at 25 KGy under controlled temperature and moisture conditions. The resultant polymer was characterized for its molecular weight according to the method described in example 1. Molecular weight after irradiation process was 45 KDa.

| | Ingredient | Amount (mg) |
|---|---|---|
| Female 2.25 ml syringe | Lactic-co-glycolic acid copolymer (N-capped) with 50% content of each of the two organic acid monomers and a molecular weight of 56 KDa, beta-irradiated as a bulk with a 25KGy dose achieving a final molecular weight of 45 KDa. | 50 |
| | Risperidone | 25 |
| Male 2.25 ml syringe | Dimethyl sulfoxide | 117 |

Risperidone particle size was characterized by light scattering and provided the following distribution of particle size: $d(0,1)=27.49$ μm, $d(0,5)=79.90$ μm and $d(0,9)=176.66$ μm.

Inherent viscosity of the irradiated polymer, as calculated by the technique described in example 1 was 0.28 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

In Vivo Plasma Levels After Intramuscular Administration to White New Zealand Rabbits The risperidone composition of this example was intramuscularly injected to White New Zealand rabbits weighing an average of 3 kg. An amount of formulation equivalent to a dose of 5 mg/kg of risperidone was intramuscularly placed in the left hind leg using a syringe with a 20 G needle. Total number of rabbits was 3. After injection, plasma levels were obtained at 0, 4 h, 1 d, 3 d, 5 d, 7 d, 10 d, 14 d, 17 d, 21 d, 24 d, 28 d, 31 d.

Figure 4:
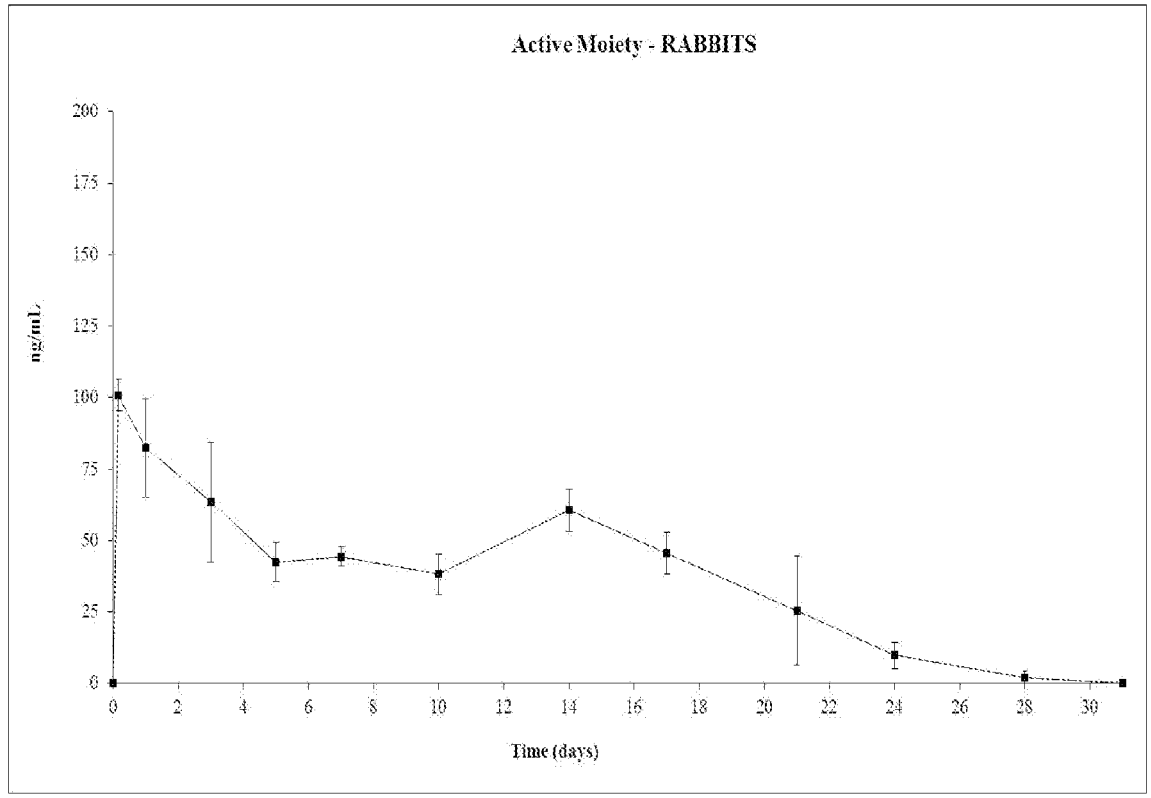
FIG. 4.—Active moiety levels profile in rabbit after the administration of the risperidone formulation described in example 4 to White New Zealand rabbits (n=3). Dose is 5 mg/kg. Results are expressed as ng/ml plasma values of active moiety versus time. The table describes Area Under the Curve (AUC) of active moiety plasma levels versus time. AUC all as well as AUC vs three different time frames are included. Units are expressed in h*ng/ml.

The kinetics of the plasma levels corresponding to the risperidone active moiety was evaluated by measuring both risperidone and its active metabolite 9-OH-risperidone in the plasma samples. The profile of the plasma levels of the risperidone active moiety and the AUC values calculated are shown in FIG. 4. The results are expressed as the addition of risperidone plus 9-OH-risperidone concentrations (ng/ml) as the function of time, since the therapeutic activity of 9-OH-risperidone is substantially equivalent to that of risperidone. As it can be observed in this FIG. 4, the injection of an amount of composition equivalent to 5 mg/kg to White New Zealand rabbits resulted again in high control of the initial burst release followed by a slow, sustained decrease, with continuous plasma levels from day 1 onwards. Once again, the plasma levels profile for the active moiety, as previously described, can be considered adequate as provide very low risk of having toxic plasma levels just after the injection.

In this example, in which rabbits were used as experimental model instead of dogs, it is not applicable the same consideration as an "adequate plasma level profile" than in Beagle dog. Rabbits exhibit a higher body temperature than Beagle dogs, about 40° C. instead of about 37-38° C. Rabbit model shows and accelerated implant degradation, and in consequence an accelerated risperidone release profile, in comparison to dog and human because that higher body temperature promotes a faster polymer degradation. This accelerated degradation of polymer does not affect the first stage of drug release profile during which implant is not degrading yet, but it leads to a faster second stage during drug is released by diffusion and degradation and it leads to a consequently shorter duration term. For that reason, in case of White New Zealand rabbit, an "adequate plasma level profile" is considered as not more than the 35% of the AUC of the active moiety (risperidone+9-OH risperidone plasma concentrations) occurring between the moment of the injection until day 7 (included), between 35% and 55% of the AUC of the active moiety occurring from day 7 and until 17 (included), and not more than 35% of the AUC of the active moiety occurring after day 17.

|  | AUC all (h * ng/ml) | $AUC_{0-7}$ days (h * ng/ml) | $AUC_{7-17}$ days (h * ng/ml) | $AUC_{17\text{-}last}$ (h * ng/ml) |
|---|---|---|---|---|
| Dose 5 mg/kg | 122924.61 | 4162.63 | 6521.64 | 2240.34 |

Example 5

Depot Formulation With Resomer® 504 Radiated to 25 KGy

In this example, a lactic-co-glycolic acid copolymer with 50% content of each of the two organic acid monomers and a molecular weight of 38 KDa was sterilized by beta irradiation at 25 KGy under controlled temperature and moisture conditions. The resultant polymer was characterized for its molecular weight according to the method described in example 1. Molecular weight after irradiation process was 28 KDa.

|  | Ingredient | Amount (mg) |
|---|---|---|
| Female 2.25 ml syringe | Lactic-co-glycolic acid copolymer (N-capped) with 50% content of each of the two organic acid monomers and a molecular weight of 38 KDa, beta-irradiated as a bulk with a 25 KGy dose achieving a final molecular weight of 28 KDa. | 50 |
|  | Risperidone | 25 |
| Male 2.25 ml syringe | Dimethyl sulfoxide. | 117 |

Risperidone particle size was characterized by light scattering and provided the following distribution of particle size: $d(0,1)=27.49$ μm, $d(0,5)=79.90$ μm and $d(0,9)=176.66$ μm.

Inherent viscosity of the irradiated polymer, as calculated by the technique described in example 1 was 0.25 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

In Vivo Plasma Levels After Intramuscular Administration to Beagle Dog:

The risperidone composition of this example was intramuscularly injected to Beagle dogs weighing an average of 10 kg. An amount of formulation equivalent to a dose of 2,5 mg/kg of risperidone was intramuscularly placed in the left hind leg using a syringe with a 20 G needle. Total number of dogs per cohort was 3. After injection, plasma levels were obtained at 0, 4 h, 1 d, 2 d, 3 d, 5 d, 7 d, 10 d, 14 d, 17 d, 21 d, 24d, and 28d.

Figure 5:
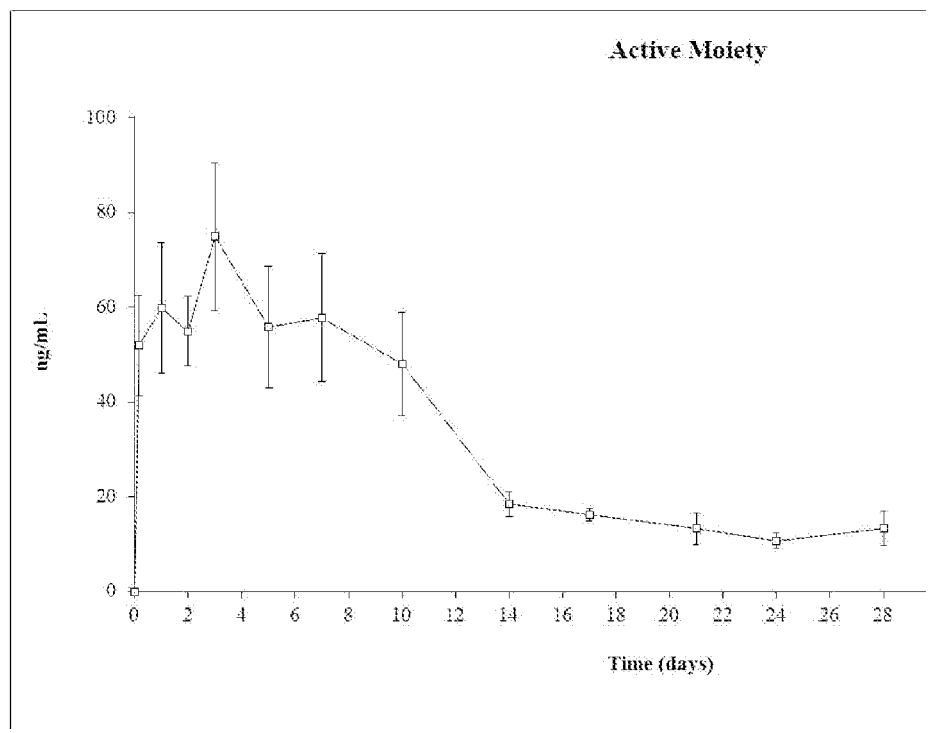
FIG. 5.—Active moiety levels profile in dog after the administration of the risperidone formulation described in example 5 to Beagle dogs (n=3). Dose is 2.5 mg/kg. Results are expressed as ng/ml plasma values of active moiety versus time. The table describes Area Under the Curve (AUC) of active moiety plasma levels versus time. AUC all as well as AUC vs three different time frames are included. Units are expressed in h*ng/ml.

The kinetics of the plasma levels corresponding to the risperidone active moiety was evaluated by measuring both risperidone and its active metabolite 9-OH-risperidone in the plasma samples. The profile of the plasma levels of the risperidone active moiety and the AUC values calculated are shown in FIG. 5. The results are expressed as the addition of risperidone plus 9-OH-risperidone concentrations (ng/ml) as the function of time, since the therapeutic activity of 9-OH-risperidone is substantially equivalent to that of risperidone. As it can be observed in this FIG. 5, the injection of an amount of composition equivalent to 2.5 mg/kg to Beagle dogs resulted in a plasma values profile that is different to the previous formulations tested. The figure shows how the formulation provides higher active moiety plasma values, probably due to a reduced control of the polymer on the release of the drug once the formulation has been injected. A reduced molecular weight could also lead to increased uptake of water throughout the time, leading to greater release of the risperidone by diffusion and to a reduced time in which the polymer hydrolizes into smaller sized soluble fractions. It is noticeable to mention that this different polymer behaviour could be obtained with a polymer with a molecular weight only 3 KDa less compared to example 2.

|  | AUC all (h * ng/ml) | $AUC_{0-7}$ days (h * ng/ml) | $AUC_{7-21}$ days (h * ng/ml) | $AUC_{21\text{-}last}$ (h * ng/ml) |
|---|---|---|---|---|
| Dose 2.5 mg/kg | 21702.82 | 10021.78 | 9662.28 | 2018.76 |

Example 6

Depot Formulation With Resomer® 503 Radiated to 15 KGy

In this example, a lactic-co-glycolic acid copolymer with 50% content of each of the two organic acid monomers and a molecular weight of 32 KDa was sterilized by beta irradiation at 15 KGy under controlled temperature and moisture conditions. The resultant polymer was characterized for its molecular weight according to the method described in example 1. Molecular weight after irradiation process was 28.3 KDa.

|  | Ingredient | Amount (mg) |
|---|---|---|
| Female 2.25 ml syringe | Lactic-co-glycolic acid copolymer (N-capped) with 50% content of each of the two organic acid monomers and a molecular weight of 32 KDa, beta-irradiated as a bulk with a 15 KGy dose achieving a final molecular weight of 28.3 KDa. | 50 |
|  | Risperidone | 25 |
| Male 2.25 ml syringe | Dimethyl sulfoxide | 117 |

Risperidone particle size was characterized by light scattering and provided the following distribution of particle size: $d(0,1)=27.49$ μm, $d(0,5)=79.90$ μm and $d(0,9)=176.66$ μm.

Inherent viscosity of the irradiated polymer, as calculated by the technique described in example 1 was 0.25 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

In Vivo Plasma Levels After Intramuscular Administration to Beagle Dog:

The risperidone composition of this example was intramuscularly injected to Beagle dogs weighing an average of 12.5 kg. An amount of formulation equivalent to a dose of 25 mg of risperidone was intramuscularly placed in the left hind leg using a syringe with a 20 G needle. Total number of dogs per cohort was 3. After injection, plasma levels were obtained at 0, 4 h, 1 d, 2 d, 3 d, 5 d, 7 d, 10 d, 14 d, 17 d, 21 d, 24 d, and 28 d.

Figure 6:
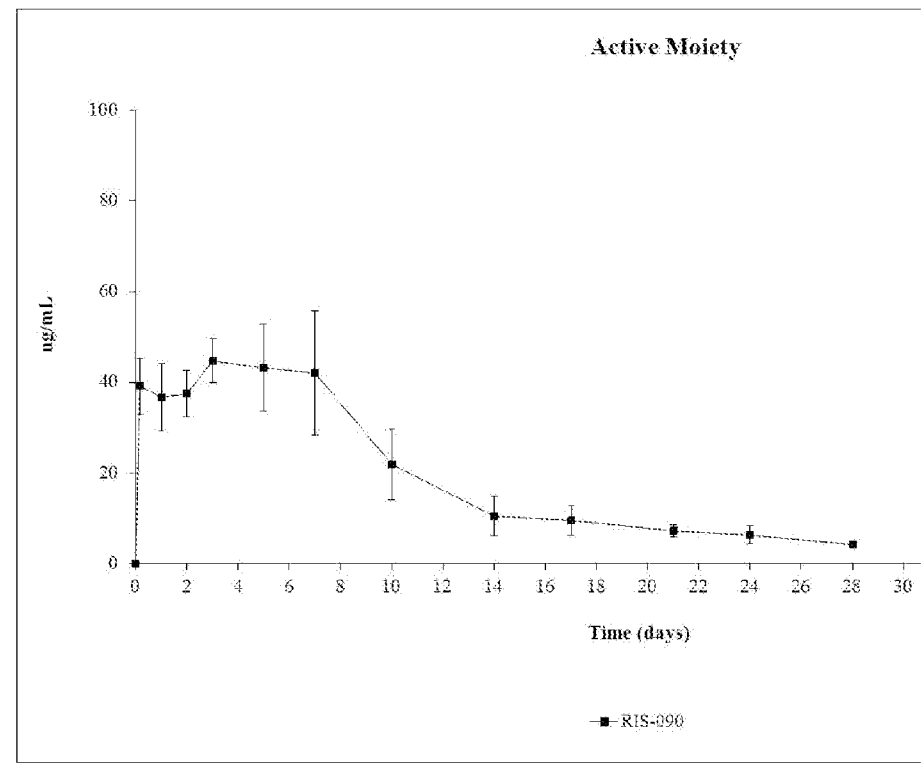
FIG. 6.—Active moiety levels profile in dog after the administration of the risperidone formulation described in example 6 to Beagle dogs (n=3). Dose is 2.0 mg/kg. Results are expressed as ng/ml plasma values of active moiety versus time. The table describes Area Under the Curve (AUC) of active moiety plasma levels versus time. AUC all as well as AUC vs three different time frames are included. Units are expressed in h*ng/ml.

The kinetics of the plasma levels corresponding to the risperidone active moiety was evaluated by measuring both risperidone and its active metabolite 9-OH-risperidone in the plasma samples. The profile of the plasma levels of the risperidone active moiety and the AUC values calculated are shown in FIG. 6. The results are expressed as the addition of risperidone plus 9-OH-risperidone concentrations (ng/ml) as the function of time, since the therapeutic activity of 9-OH-risperidone is substantially equivalent to that of risperidone. As it can be observed in this Figure, the result was similar to what it was obtained in example 5. This time, the reduction of molecular weight from the original is only 3.7 KDa, smaller to that observed in examples 2, 3 and 4. This is important to notice, as it could had been thought that the more irregular plasma levels profile obtained in example 5 was mostly due to an intense reduction in the polymer molecular weight, potentially leading to an increased heterogeneity in the distribution of the different sized chains. This example shows how the molecule can be tailored to a specific molecular weight distribution and to obtain similar plasma levels profile.

|  | AUC all (h * ng/ml) | $AUC_{0-7}$ days (h * ng/ml) | $AUC_{7-21}$ days (h * ng/ml) | $AUC_{21-last}$ (h * ng/ml) |
|---|---|---|---|---|
| Dose 2 mg/kg | 13245.14 | 6873.74 | 5371.44 | 999.96 |

Example 7

Depot Formulation With Resomer® 504 Without Radiation

|  | Ingredient | Amount (mg) |
|---|---|---|
| In this example, a lactic-co-glycolic acid copolymer with 50% content of each of the two organic acid monomers and a molecular weight (according to method described in example 1) of 48 KDa was used. Female 2.25 ml syringe | Lactic-co-glycolic acid copolymer (N-capped) with 50% content of each of the two organic acid monomers and a molecular weight of 48 KDa. | 50 |
|  | Risperidone | 25 |
| Male 2.25 ml syringe | Dimethyl sulfoxide | 117 |

Risperidone particle size was characterized by light scattering and provided the following distribution of particle size: d(0,1)=27.49 µm, d(0,5)=79.90 µm and d(0,9)=176.66 µm.

Inherent viscosity of the irradiated polymer, as calculated by the technique described in example 1 was 0.33 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

In Vivo Plasma Levels After Intramuscular Administration to Beagle Dog:

The risperidone composition of this example was intramuscularly injected to Beagle dogs weighing an average of 12.5 kg. An amount of formulation equivalent to a dose of 25 mg of risperidone was intramuscularly placed in the left hind leg using a syringe with a 20 G needle. Total number of dogs per cohort was 3. After injection, plasma levels were obtained at 0, 4 h, 1 d, 2 d, 3 d, 5 d, 7 d, 10 d, 14 d, 17 d, 21 d, 24 d, and 28 d.

Figure 7:
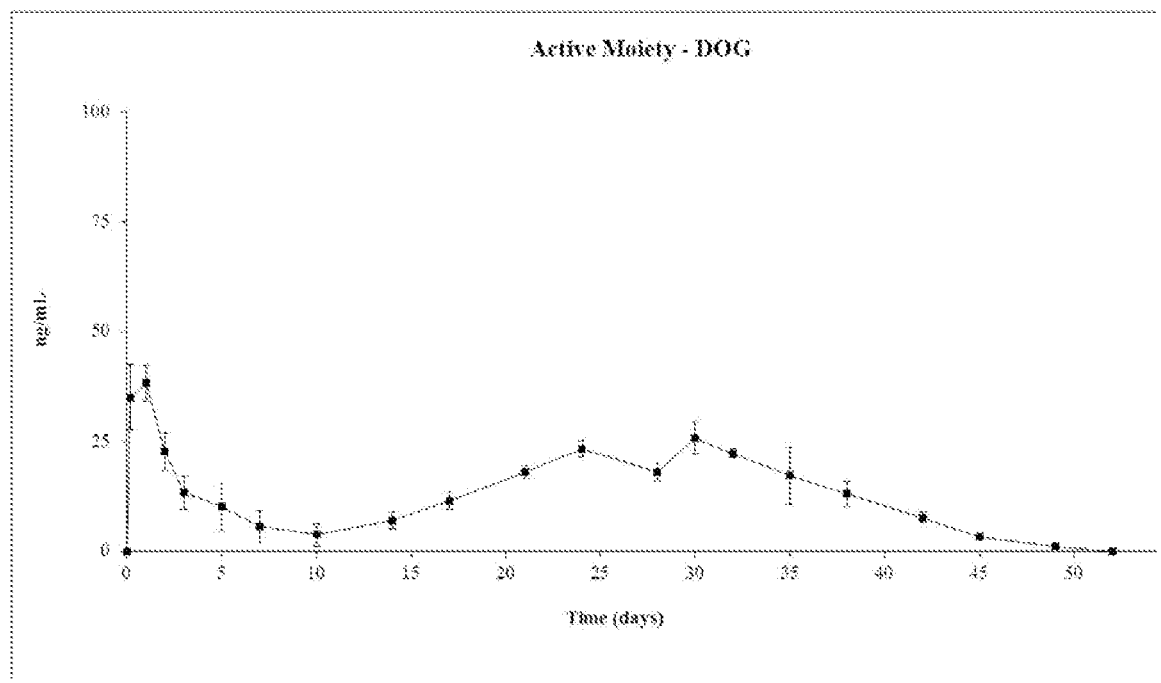
FIG. 7.—Active moiety levels profile in dog after the administration of the risperidone formulation described in example 7 to Beagle dogs (n=3). Dose is 2.0 mg/kg. Results are expressed as ng/ml plasma values of active moiety versus time. The table describes Area Under the Curve (AUC) of active moiety plasma levels versus time. AUC all as well as AUC vs three different time frames are included. Units are expressed in h*ng/ml.

The kinetics of the plasma levels corresponding to the risperidone active moiety was evaluated by measuring both risperidone and its active metabolite 9-OH-risperidone in the plasma samples. The profile of the plasma levels of the risperidone active moiety and the AUC values calculated are shown in FIG. 7. The results are expressed as the addition of risperidone plus 9-OH-risperidone concentrations (ng/ml) as the function of time, since the therapeutic activity of 9-OH-risperidone is substantially equivalent to that of risperidone. The figure shows the effect of using a polymer with a molecular weight that is higher than the range valid for this formulation. Initial plasma values do not change in a significant way, as risperidone solubility in the DMSO and DMSO diffusion towards surrounding liquids are the major factors controlling the release of risperidone from the implant. Then, it can be seen how a reduced release by diffusion leads to a reduction in plasma levels of active moiety. The higher molecular weight chains of the polymer also increases the time required to release the risperidone by the formation of reduced molecular weight soluble polymer molecules by hydrolysis. This fact is detected in the active moiety plasma levels profile as a delayed peak.

|  | AUC all (h * ng/ml) | $AUC_{0-7}$ days (h * ng/ml) | $AUC_{7-21}$ days (h * ng/ml) | $AUC_{21-last}$ (h * ng/ml) |
|---|---|---|---|---|
| Dose 2 mg/kg | 15601.88 | 2902.28 | 2935.32 | 9764.28 |

Example 8

Depot Formulation With Resomer® 504 Radiated to 25 KGy

The current example demonstrates the concept is also valid to achieve an intramuscularly injectable paliperidone formulation suitable to be administered once each 4 weeks.

A lactic-co-glycolic acid copolymer with 50% content of each of the two organic acid monomers and a molecular weight of 50 KDa was sterilized by beta irradiation at 25 KGy under controlled temperature and moisture conditions. The resultant polymer was characterized for its molecular weight according to the method described in example 1. Molecular weight after irradiation process was 35 KDa.

| | Ingredient | Amount (mg) |
|---|---|---|
| Female 2.25 ml syringe | Lactic-co-glycolic acid copolymer (N-capped) with 50% content of each of the two organic acid monomers and a molecular weight of 50 KDa, beta-irradiated as a bulk with a 25KGy dose achieving a final molecular weight of 35 KDa. | 50 |
| | Paliperidone | 25 |
| | Dimethyl sulfoxide | 117 |

Paliperidone particle size was characterized by light scattering and provided the following distribution of particle size: d(0,1)=17.41 μm, d(0,5)=51.61 μm and d(0,9)=175.32 μm.

Inherent viscosity of the irradiated polymer, as calculated by the technique described in example 1 was 0.28 dl/g.

The paliperidone implantable formulation was prepared by connecting male and female syringes and moving the plungers forwards and backwards upon complete dissolution of the polymer and the formation of a homogeneous suspension of the paliperidone in the polymer dissolution.

In Vivo Plasma Levels After Intramuscular Administration to Beagle Dog:

The paliperidone composition of this example was intramuscularly injected to Beagle dogs weighing an average of 10 kg. An amount of formulation equivalent to a dose of 1.5 mg/kg of risperidone was intramuscularly placed in the left hind leg using a syringe with a 20 G needle. Total number of dogs per cohort was 3. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d, 42 d, 45 d, 49 d, 52 d, 56 d, 59 d, 63 d, 70 d, 77 d.

Figure 8:
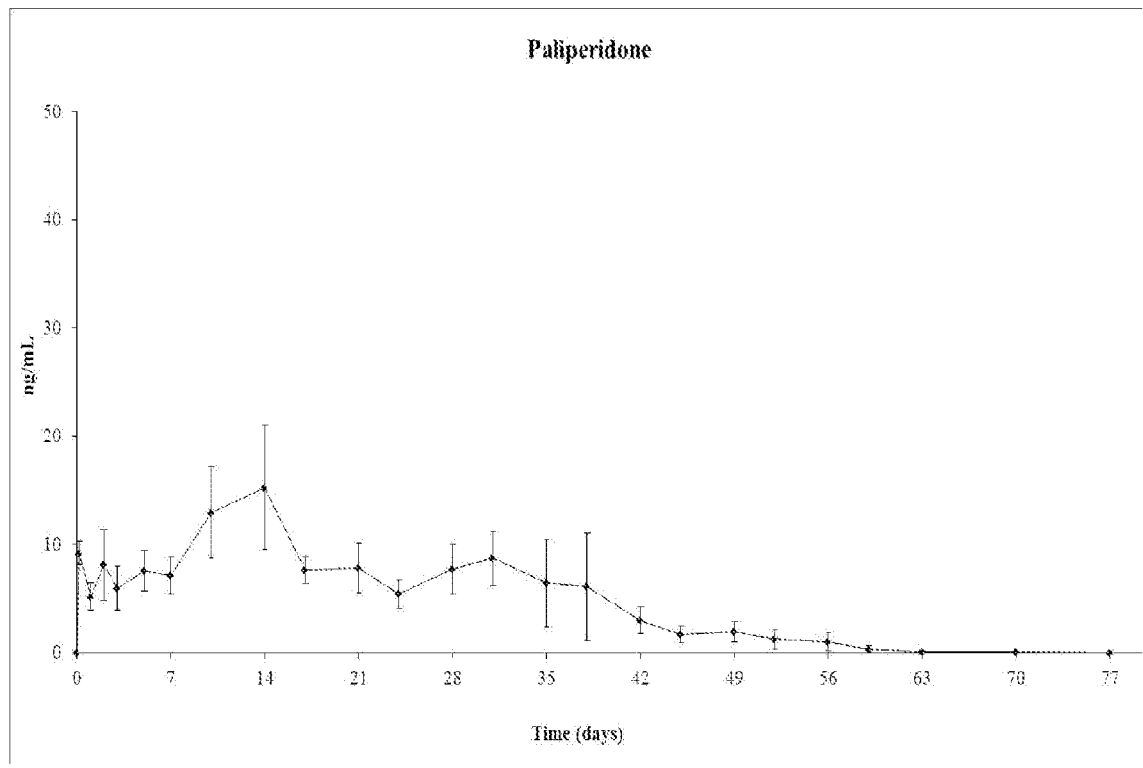
FIG. 8.—Paliperidone levels profile in dog after the administration of the paliperidone formulation described in example 8 to Beagle dogs (n=3). Dose is 1.5 mg/kg. Results are expressed as ng/ml plasma values of paliperidone versus time. The table describes Area Under the Curve (AUC) of paliperidone plasma levels versus time. AUC all as well as AUC vs three different time frames are included. Units are expressed in h*ng/ml.

The kinetics of the plasma levels corresponding to the paliperidone was evaluated and and the AUC values calculated are shown in FIG. 8. The results are expressed as paliperidone concentrations (ng/ml) as the function of time. As it can be observed in this Figure, the injection of an amount of composition equivalent to 1.5 mg/kg to Beagle dogs resulted again in very high control of the initial burst release followed by a continuous paliperidone plasma level profile during 59 days. The difference in the release properties compared to the same risperidone formulation can be related to different pKa values of both drugs that can affect the in vivo biodegradation properties of the polymer and produce release of the drug over a longer period of time. The formulation tested demonstrates the feasibility of the composition to obtain a paliperidone formulation that can provide prolonged release of paliperidone during an entire month and can be administered each 4 weeks or even each longer times.

| | AUC all (h * ng/ml) | $AUC_{0-7}$ days (h * ng/ml) | $AUC_{7-21}$ days (h * ng/ml) | $AUC_{21-last}$ (h * ng/ml) |
|---|---|---|---|---|
| Dose 1.5 mg/kg | 8636.94 | 1160.34 | 3630.84 | 3845.76 |

Additional Disclosure

Additional parameters such as the mass ratio between the amounts of polymeric solution (polymer+solvent) and drug, and the solvent/drug mass ratio, can also be useful to provide control over the initial release of risperidone from the compositions of the invention.

A first aspect of the invention provides an injectable depot composition, comprising:

a. a drug, such as is risperidone and/or its metabolites or prodrugs in any combination thereof,
b. at least a biocompatible polymer which is a copolymer comprising lactic acid and glycolic acid monomers, wherein the monomers are present at a monomer ratio of lactic to glycolic acid in the range from about 48:52 to about 77:23., and
c. at least a water-miscible solvent with a dipole moment about 3.9-4.3 D, wherein the solvent and polymer form a polymer solution having a viscosity in the range of 0.5 to 3.0 Pa·s, and the solvent/drug mass ratio ranges from about 10:1 to about 4:1, characterised in that the drug/polymer mass ratio is between 25 and 35% expressed as the weight percentage of the drug with respect of the drug plus polymer.

In some embodiments, the concentration of the polymeric component in the injectable composition is in the range of about 25-50%, (expressed as the percentage of polymer weight based on total polymeric solution component) and or about 30-40%.

In some embodiments, the injectable composition has a viscosity in the range of about 0.5-7.0 Pa·s, more preferably about 0.5-3.0 Pa·s, and most preferably about 0.7-3.0 Pa·s.

In some embodiments, the compositions of the invention comprise a biodegradable poly(L-lactide-co-glycolide) copolymer (PLGA) matrix. The monomer ratio of lactic acid to glycolic acid monomers present in the polymer can range from about 45:65 to about 75:25, about 50:50 to about 75:25, about 50:50 to about 70:30, about 50:50 to about 65:35, or about 65:35 to about 75:25. In some embodiments, the intrinsic or inherent viscosity of the polymer is in the range of about 0.16 to about 0.60 dl/g when measured in chloroform at 25° C. and a 0.1% (wt/v) concentration. In some embodiments, the PLGA copolymer is end-capped. In some embodiments, the PLGA copolymer is irradiated with beta-radiation prior to inclusion in the injectable composition. In some embodiments, a commercially available PLGA copolymer has an initial intrinsic viscosity that is to high for use but after irradiation with beta-radiation it has an intrinsic viscosity that is within the ranges specified herein thereby rendering it suitable for use in the injectable composition.

The invention also provides an injectable composition that forms a single solid body implant in a subject to which it is administered, the composition comprising:

a. a polymeric solution comprising a biodegradable poly(L-lactide-co-glycolide) polymer having a monomer ratio of lactic acid to glycolic acid in the range of 50:50 to 75:25, and a solvent having a dipole moment in the range of 3.9-4.3 D, wherein the solvent is present in an amount sufficient to dissolve the polymer; and
b. drug-containing particles of risperidone, a metabolite of risperidone, a prodrug of risperidone or a combination thereof at least partially dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution is in the range of about 60-130 microns; wherein
c. the intrinsic or inherent viscosity of the polymer is in the range of about 0.16 to about 0.60 dl/g when measured in chloroform at 25° C. and a 0.1% concentration;
d. the viscosity of the polymeric solution is in the range of about 0.5-7.0 Pa·s;

e. the concentration of drug in the injectable composition is in the range of about 4 and 16 wt %, expressed as the percentage of the drug with respect to the total composition weight, or the mass ratio of the amount of polymeric solution (polymer+solvent) to the amount of drug in the injectable composition ranges from about 15:1 to 5:1;

f. the concentration of polymer in the injectable composition is in the range of about 25-50% expressed as the percentage of polymer weight based on total polymeric solution component; and g. the composition has a solvent/drug mass ratio ranging from about 10:1 to about 4:1.

Embodiments of the invention include those wherein: a) the risperidone is present in solid form in the container prior to mixing with the solvent; b) the risperidone is present in particulate form or as a lyophilisate in the container prior to mixing with the solvent; c) the particle size distribution of the risperidone is as follows: not more than 10% of the total volume of drug particles are less than 10 microns in size and not more than 10% of the total volume of drug particles are greater than 225 microns in size; d) the d0.5 of the particle size distribution is in the range of about 60-130 microns; e) the mass ratio of the amount of polymeric solution (polymer+solvent) and to the amount of risperidone in the injectable composition ranges from about 15:1 to 5:1; f) the mass ratio of the amount of solvent and the amount of risperidone (mg solvent/mg risperidone) in the injectable composition ranges from about 12:1 to 4:1; g) the kit further comprises an alkaline agent; h) the mole ratio of risperidone to alkaline agent ranges from 2/3 to 2/5; i) the solvent, polymeric solution, risperidone and/or injectable composition is sterilized prior to administration; and/or j) the kit further comprises an alkaline agent in either or both containers.

In some embodiments, the invention provides a process for preparing an injectable composition, comprising: a) dissolving a polymer having a molecular weight greater than about 15 KDa in a solvent having a dipole moment about 3.9-4.3 D to form a polymeric solution having a viscosity greater than about 0.5 Pa·s, wherein the concentration of the polymer in the solution is in the range of about 25-50%, expressed as the percentage of polymer weight based on total solution weight, wherein the polymer comprises lactic acid and glycolic acid monomers, wherein the monomers are present at a monomer ratio of lactic acid to glycolic acid in the range of about 50:50 to 75:25; and b) subjecting the polymer to at least 10 KGy of β-irradiation to degrade at least a portion of the polymer thereby reducing its molecular weight to a range of about 25-52 KDa and reducing the viscosity of a respective polymeric solution thereof to a range of about 0.5 to 3.0 Pa·s. In some embodiments, drug is included in the polymeric solution, and the weight percentage of drug with respect to the total weight of drug plus polymer is in the range of about 25 to 35%.

Another factor contributing to controlling the initial release of drug from the implant is the risperidone/polymer mass ratio of the injectable composition. In some embodiments, this mass ratio, expressed as the percentage of the drug weight with respect to total weight of the drug plus polymer, is in the range of about 15-40% weight, more preferably about 25-35% wt, and most preferably about 33% wt.

In some embodiments, the mass ratio of the amount of polymeric solution (polymer+solvent) to the amount of risperidone in the injectable composition ranges from about 15:1 to 5:1, more preferably from about 12:1 to 5:1 and most preferably from about 7:1 to 6.5:1. In the most preferred embodiments, this mass ratio is about 6.66:1.

In some embodiments, the mass ratio of the amount of solvent and the amount of risperidone (mg solvent/mg risperidone) in the injectable composition ranges from about 12:1 to 4:1, more preferably about 10:1 to 4:1 and most preferably about 5:1 to 4:1. In the most preferred embodiments, this mass ratio is about 4.66:1.

The invention also provides an injectable composition that forms a single solid body implant in a subject to which it is administered, the composition comprising:

a. a polymeric solution comprising a biodegradable poly (L-lactide-co-glycolide) polymer having a monomer ratio of lactic acid to glycolic acid in the range of 50:50 to 75:25, and a solvent having a dipole moment in the range of 3.9-4.3 D; and b. drug-containing particles of risperidone, a metabolite of risperidone, a prodrug of risperidone or a combination thereof dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution being in the range of about 60-130 microns; wherein c. the composition has a solvent/drug mass ratio ranging from about 10:1 to about 4:1.

Yet another factor contributing to controlling the initial release of drug from the implant is the drug's particle size. Large particles provide a smaller surface area per weight thereby reducing the initial release (burst) but the release may be then delayed until the beginning of the degradation of the polymeric matrix. On the other hand, small particles evoke higher burst levels due to increased surface area and easier drug diffusion from small particles during implant hardening, followed by continuous drug release levels due to the combination of the processes of drug diffusion and implant erosion. Consequently, in a preferred embodiment of the invention a wide particle size distribution, combining large and small particle sizes in different ratios, is used in order to reduce the initial burst and still maintain a suitable constant drug release by diffusion of smaller particles during the first phase of release and gradual release of drug from the bigger particles while the polymer degrades, i.e. during the period of time (days to weeks) following the initial burst phase. In some embodiments, the particle size distribution of the drug is as follows: not more than 10% of the total volume of drug particles are less than 10 microns in size (equivalent diameter in volume as a function of applying Fraunhofer theory to irregularly shape particles; as measured by laser light scattering, such as with a Malvern Mastersizer 2000) and not more than 10% of the total volume of drug particles are greater than 225 microns in size. In addition, the drug particles possess a d0.5 value preferably in the range of about 60-130 microns. Accordingly, in some embodiments, the risperidone comprises a broad particle size distribution, which can be monomodal, bimodal or trimodal.

The risperidone-implantable formulations were prepared by completely dissolving the polymer in the solvent and subsequently suspending the drug in said polymeric solution. The following different risperidone particle size distributions were evaluated for the same formulation:

25-350 microns: d0.1, 25 microns and d0.9, 350 microns (not more than 10% of drug particles with a particle size smaller than 25 microns, and not more than 10% particles larger than 350 microns)

25-225 microns: d0.1 of 25 microns and d0.9 of 225 microns (not more than 10% of drug particles with a particle size smaller than 25 microns, and not more than 10% particles larger than 225 microns)

90-150 microns: sieved between 90-150 microns 45-90 microns: sieved between 45-90 microns milled, <10 microns: drug milled to d0.9 10 microns (not more than 10% particles larger than 10 microns).

The compositions of the invention comprise at least a polymer or polymer matrix, a solvent and a drug. The polymer is preferably a biocompatible and biodegradable polymer or polymer matrix. In order not to cause severe damage to the body following administration, the preferred polymers are biocompatible, non-toxic for the human body, not carcinogenic, and do not induce significant tissue inflammation. The polymers are preferably biodegradable in order to allow natural degradation by body processes, so that they are readily disposable and do not accumulate in the body. In selecting the appropriate grade of PLGA copolymer, the time required for degradation of PLGA is related to the monomer ratio used in production: the higher the content of glycolide units, the lower the time required for degradation. In addition, polymers that are end-capped with esters (as opposed to the free carboxylic acid) demonstrate longer degradation half-lives. The preferred polymers are selected from end-capped terminal carboxylic poly-lactide and poly-glycolic acid copolymers (PLGA) mixed in a ratio from 50:50 to 75:25 (ratio of lactic acid monomer to glycolic acid monomer), with an intrinsic or inherent viscosity preferably in the range of 0.16-0.60 dl/g, and more preferably between 0.25-0.48 dl/g, as measured in chloroform at 25° C. and at a concentration of 0.1% wt/v with a Ubbelohde size 0c glass capillary viscometer (RESOMER® grades) or as measured in chloroform at 30° C. and at a concentration of 0.5% wt/v with a size 25 Cannon-Fenske glass capillary viscometer (LAKESHORE MATERIALS™ grades). In some embodiments, the PLGA copolymer has a lactic acid to glycolic acid monomer ratio ranging from 48:52 to 52:48 or 48:52 to 77:23.

As used herein, the term "polymeric solution" is taken to mean the fluid composition comprising a combination of the solvent and the polymer dissolved therein. In some embodiments, at least 80%, at least 90%, at least 95%, at least 99% or all of the polymer is dissolved in the solvent. If not otherwise specified, the viscosity value of the polymeric solution or the injectable composition is given in Pa·s units, measured in chloroform at 25° C. and at concentration of 0.1% wt/v.

In some embodiments, the drug is completely dissolved, partially dissolved or completely undissolved in the solvent used to form the polymeric solution to form the injectable composition. The drug is preferably at least partly suspended, i.e. only partially dissolved, in the solvent or polymeric solution. In some embodiments, ≤5%, ≤10%, ≤20%, ≤30%, ≤40%, ≤50%, ≤60%, ≤70%, ≤80%, ≤90%, ≤95% or ≤99% wt of the drug is dissolved in the solvent or polymeric solution to form the injectable composition. In some embodiments, ≥1%, ≥5%, ≥10%, ≥20%, ≥30%, ≥40%, ≥50%, ≥60%, ≥70% or up to about 80% wt. of the drug is dissolved in the solvent or polymeric solution to form the injectable composition.

In some embodiments, the concentration of drug in the injectable composition is generally in the range of about 4 and 16 wt %, expressed as the percentage of the drug with respect to the total composition weight. More preferably, the drug content is between 7 and 15% wt, and most preferably about 13% wt with respect to the total composition weight.

One of the factors contributing to controlling the initial release of drug from the implant, after placement in an aqueous environment, is the viscosity of the polymeric solution of the injectable composition. The term "polymeric solution" is defined as the combination of the polymer matrix and the solvent in which it is dissolved. In some embodiments, the polymeric solution has a viscosity in the range of about 0.5-7.0 Pa·s, more preferably about 0.5-3.0 Pa·s, and most preferably about 0.7-3.0 Pa·s.

Another factor contributing to controlling the initial release of drug from the implant is the risperidone/polymer mass ratio of the injectable composition. In some embodiments, this mass ratio, expressed as the percentage of the drug weight with respect to total weight of the drug plus polymer, is in the range of about 15-40% weight, more preferably about 25-35% wt, and most preferably about 33% wt.

The plasma concentration profile during the dosing period can exhibit one, two, or more maxima and one, two or more minima. An initial maximum can be caused by dissolution of risperidone during the initial day(s) of the dosing period followed by a slowing of the release thereof and another maximum can be caused by increased rate of release during the remaining days of the dosing period. Embodiments of the invention include those wherein: a) the plasma profile exhibits a maximum during the initial one to three days or one to two days of the dosing period; b) the plasma profile exhibits a maximum during the latter 11 to 13 days or 12 to 14 days of the dosing period; c) the plasma profile exhibits a maximum during the initial days of the dosing period and a maximum during the remaining days of the dosing period; or d) the plasma profile is substantially level (within ±20%, ±15%, ±10% or ±5% of the average or mean) during the dosing period.

Embodiments of the invention include those wherein: a) the molecular weight of the polymer is greater before irradiation than it is after irradiation; b) the molecular weight of the polymer is greater than 15 KDa before irradiation; c) the molecular weight of the polymer is in the range of 15-60 KDa, 25-52 KDa or 28-43KDa after irradiation; d) the viscosity of a polymeric solution containing polymer that has not been irradiated is greater than about 0.5 Pa·s; e) the viscosity of a polymeric solution containing polymer that has been irradiated is in the range of 0.5-7.0 Pa·s, 0.5-3.0 Pa·s or 0.7 to 2.0 Pa·s.; and/or f) the sufficient amount of radiation is at least 10, at least 15, at least 20 or at least 25 KGy.

The mass ratio of the amount of solvent to the amount of risperidone (mg solvent/mg risperidone) in the injectable composition ranges may also contribute toward controlling the initial release of drug from the implant. In some embodiments, the mass ratio of the amount of solvent and the amount of drug (mg solvent/mg drug) in the injectable composition ranges from about 12:1 to about 1.5:1, about 10:1 to about 1.5:1 or about 5:1 to about 1.5:1. In some embodiments, this mass ratio is about 4.66:1, as described in the examples below.

The mass ratio of the amount of polymeric solution to the amount of drug in the injectable composition ranges may also contribute toward controlling the initial release of drug from the implant. In some embodiments, the mass ratio ranges from about 24:1 to about 1.5:1, about 12:1 to about 2:1, about 7:1 to about 2.5:1 or about 6.7:1 to about 3:1. In some embodiments, this mass ratio is about 6.66:1, as described in the examples below.

Embodiments of the invention include those wherein: a) the drug is selected from the group consisting of fentanyl, olanzapine, risperidone and letrozole; b) the solvent is selected from the group consisting of DMSO and NMP; c) the polymer is selected from the group consisting of poly (lactic acid), poly(lactic acid-co-glycolic acid) copolymer and a combination thereof; d) the monomer ratio of the poly(lactic acid-co-glycolic acid) copolymer is in the range of about 48:52 to 100:0, and the copolymer has an inherent or intrinsic viscosity in the range of about 0.16-0.60 dl/g measured in chloroform at 25° C. and at a concentration of 0.1% wt; e) the polymer has an inherent or intrinsic viscosity in the range of about 0.20-0.50 dl/g or 0.25-0.48 dl/g, measured in chloroform at 25° C. and 0.1% concentration wt/v; f) the concentration of polymer in the injectable composition is in the range of about 20 to about 50%, about 25 to about 40%, or about 30 to about 40%, expressed as the percentage of polymer weight based on total weight of injectable composition; g) the viscosity of the injectable composition is in the range of about 0.5-7.0 Pa·s, about 0.5-4.0 Pa·s, or about 0.7-4.0 Pa·s; h) the drug (or metabolite or prodrug thereof) has a particle size where not more than 10% of the total volume of the particles is less than the range 0.1-10 μm, 0.5-10 μm or 1-10 μm, not more than the 10% of the total volume of particles is greater than the range 225-1000 μm, 225-700 μm or 225-400 μm, respectively, and the d0.5 of the size distribution is in the range of about 10-1000 μm, 20-700 μm or 40-200 μm, respectively, i) the ratio of solvent to polymer is in the range of about 4:1 to about 1:1, about 3:1 to about 1.2:1, or about 2:1 to about 1.4:1; k) the composition is injectable by hand with a syringe through a 18-22 gauge or 20-21 gauge needle; and/or I) the polymeric solution excluding drug has a viscosity in the range of about 0.5 to 3.0 Pa·s or 0.7 to 3.0 Pa·s.

Embodiments of the invention include those wherein: a) the drug is soluble, partially soluble or insoluble in the solvent; b) the solubility of the drug in the solvent is about 90 mg/ml or less, about 65 mg/ml or less, or about 10 mg/ml or less; c) a minor portion, a major portion or none of the drug is present in particulate form in the injectable composition; d) the particle size distribution of the drug expressed as volume is as follows: d0.9 about 150-400 μm, d0.5 about 40-200 μm and d0.1 about 10-60 μm; e) the mass ratio of solvent to drug is in the range of about 10:1 to about 1.5:1 f) the concentration of drug in the injectable composition is in the range of about 4% to about 40% wt or about 4% to about 25%, expressed as the percentage of the drug with respect to the total composition weight; g) the drug is present as particles, is partially dissolved in or is completely dissolved in the injectable composition prior to administration; h) the mass ratio of the amount of polymeric solution (polymer+solvent) to the amount of drug in the injectable composition ranges from about 24:1 to about 1.5:1 or about 15:1 to about 3:1.

The polymer or polymer matrix is preferably a biocompatible and biodegradable polymer matrix. In order not to cause any severe damage to the body following administration, the preferred polymers are biocompatible, non-toxic for the human body, not carcinogenic, and do not induce significant tissue inflammation. The polymers are preferably biodegradable in order to allow natural degradation by body processes, so that they are readily disposable and do not accumulate in the body. In selecting the appropriate grade of PLGA copolymer, the time required for degradation of PLGA is related to the monomer ratio used in production: the higher the content of glycolide units, the lower the time required for degradation. In addition, polymers that are end-capped with esters (as opposed to the free carboxylic acid) demonstrate longer degradation half-lives. The preferred polymers are selected from end-capped terminal carboxylic poly-lactide and poly-glycolic acid copolymers mixed in a ratio from 48:52 to 100:0, with an inherent or intrinsic viscosity preferably in the range of 0.16-0.60 dl/g, and more preferably between 0.20-0.50 dl/g as measured in chloroform at 25° C. at a concentration of 0.1% wt/v with a Ubbelohde size 0c glass capillary viscometer (RESOMER® grades) or as measured in chloroform at 30° C. and at a concentration of 0.5% wt/v with a size 25 Cannon-Fenske glass capillary viscometer (LAKESHORE MATERIALS™ grades). The concentration of the polymeric component in the compositions of the invention is preferably in the range of about 20-50%, (expressed as the percentage of polymer weight based on total polymeric solution component) and more preferably in the range of about 25 to about 40%. Suitable grades of PLGA copolymers as described herein (according to molecular weight, intrinsic viscosity and/or molar ratio of lactic acid monomer to glycolic acid monomer) are end-capped (such as with an ester group, e.g. lauryl ester, methyl ester) are available from EVONIK® (Essen, Germany), Boehringer Ingelheim (Ingelheim am Rhein, Germany), ALKERMES (Dublin, Ireland) or SIGMA ALDRICH (ST. Louis, Mo.) and are marketed under the tradenames RESOMER®, LAKESHORE BIOMATERIALS™, or MEDISORB®. As the composition of some grades of end-capped PLGA is proprietary, the identity of the ester end-cap is not publicly available. Nonetheless, the performance properties of the grades of PLGA copolymer described herein are known and are used to characterize the material.

The initial release of drug from the implant can be controlled by varying the drug/polymer mass ratio of the injectable composition. In some embodiments, this mass ratio, expressed as the percentage of the drug weight with respect to total weight of the drug plus polymer, is in the range of about 15-50% weight, more preferably about 25-50% wt, and most preferably about 33-45% wt.

Embodiments of the invention include those wherein: a) the composition is administered every two weeks, every three weeks, every four weeks or every five weeks during a treatment period; b) the composition provides a therapeutic plasma level of drug or other form thereof from within 24 hours after administration to at least 14 days or at least four weeks after administration; c) the plasma level of active moiety (risperidone+9-OH risperidone) ranges from about 5 to about 150 ng/ml and preferably from about 10 to about 100 ng/ml in the steady state during a dosing period; d) the implant provides an active moiety (risperidone+9-OH risperidone) plasma level within the range of about 5 to about 80 ng/ml when about 116 to about 700 mg, respectively, of the composition comprising about 25 to about 150 mg, respectively, of risperidone are administered via injection; e) the injectable composition is exposed to an aqueous fluid thereby forming a solid body which is then administered to a subject in need thereof; f) the injectable composition is formed within one month, within three weeks, within two weeks, within one week, within three days, within one day, within less than one day, within 18 hours, within 12 hours, within 6 hours, within 1 hour, within 15 minutes or within 5 minutes prior to administration to a subject; g) the injectable composition is warmed or cooled prior to administration to a subject; h) the polymer, solvent polymer solution and/or drug is sterilized prior to administration; i) sterilization comprises sterilization of the drug or polymer by exposure to beta-irradiation in the range 5-25 KGy; j) sterilization comprises sterilization of the polymer solution by filtration through a filtration medium having a nominal pore size of 0.22 microns or less; k) the composition is administered intramuscularly, intraperitoneally, intrathecally, intravaginally, subcutaneously, intracranially or intracerebrally. Some individual subjects may, on an equivalent dose basis, exhibit plasma concentrations outside the ranges specified herein for reasons such as poor health, advanced age, compromised metabolism, renal failure, disease, etc. Even so, a majority of subjects in a patient population to which the injectable implant is administered will exhibit plasma concentrations with those specified herein.

In some embodiments, the injectable depot composition is sterile as a finished product. The biocompatible polymer can be sterilized prior to its aseptic filling process, preferably by an aseptic filling process by beta-irradiation in the range 5-25 KGy or it can be sterilized after being dissolved in a solvent to form a polymeric solution followed by filtration of the polymeric solution through a filter with a 0.22 μm pore size or less. Alternatively, the drug and/or the biocompatible polymer of the composition may be subjected to terminal sterilization processes, preferably by beta-irradiation in the range 5-25 KGy.

In some embodiments, the invention provides a process for preparing an injectable composition as described herein, the process comprising: a) subjecting a PLGA polymer to a sufficient amount of β-irradiation to degrade at least a portion of the polymer thereby reducing its molecular weight; and b) dissolving the polymer in a solvent to form a polymeric solution having a desired viscosity. In some embodiments, a mixture of drug and PLGA polymer are exposed to beta-irradiation prior to addition of the solvent, which would result in formation of a sterilized injectable composition of the invention.

The implant of the invention can provide substantially improved plasma levels of drug during the initial one to three days after administration when compared to another injectable formulation (not according to the invention) containing the same drug when administered on an equivalent dose basis.

In humans, the average plasma concentration of risperidone can range from about 3-200, about 5-80, or about 10-60 ng/ml when an amount of injectable composition equivalent to a dose of about 25-150, about 37.5-125, or about 50-100 mg of risperidone is administered. The average Cmin during the dosing period is in the range of about 1-80, 5-50, or about 5-40 ng/ml when an amount of injectable composition equivalent to a dose of about 25-150, about 37.5-125, or about 50-100 mg, respectively, of risperidone is administered. The average Cmax during the dosing period is in the range of about 8-300, 10-150, or 10-120 ng/ml when an amount of injectable composition equivalent to a dose of 25-150, 37.5-125, or 50-100 mg, respectively, of risperidone is administered. Some individual subjects may, on an equivalent dose basis, exhibit plasma concentrations outside the ranges specified herein for reasons such as poor health, advanced age, compromised metabolism, renal failure, disease, etc. Even so, a majority of subjects in a patient population to which the injectable implant is administered will exhibit plasma concentrations with those specified herein.

As used herein, whenever the plasma concentration of a drug is mentioned, such plasma concentration includes within it the sum total of the plasma concentration of the drug and its active metabolite(s). For example, whenever the plasma concentration of risperidone is mentioned, such plasma concentration includes within it the sum total of the plasma concentrations of risperidone and its active metabolite(s), such as 9-OH-risperidone (paliperidone).

Embodiments of the invention include those wherein: a) the molecular weight of the polymer is greater before irradiation than it is after irradiation; b) the molecular weight of the polymer is greater than 10 KDa before irradiation; c) the molecular weight of the polymer is in the range of 10-60 KDa, 10-52 KDa or 10-43KDa after irradiation; d) the viscosity of a polymeric solution containing polymer that has not been irradiated is greater than about 0.5 Pa·s; e) the viscosity of a polymeric solution containing polymer that has been irradiated is in the range of 0.5-7.0 Pa·s, 0.5-3.0 Pa·s or 0.7 to 2.0 Pa·s.; and/or f) the sufficient amount of radiation is at least 10, at least 15, at least 20 or at least 25 KGy.

The invention according to the above wherein the drug, and/or metabolite and/or prodrug is present as particles having a particle size distribution as follows:
a) not more than 10% of the total volume of the particles is less than the range 0.1-10 μm, not more than the 10% of the total volume of particles is greater than the range 225-1000 μm, and the d0.5 of the size distribution is in the range of about 10-1000 μm;
b) not more than 10% of the total volume of the particles is less than the range 0.5-10 μm, not more than the 10% of the total volume of particles is greater than the range 225-700 μm, and the d0.5 of the size distribution is in the range of about 20-700 μm; or
c) not more than 10% of the total volume of the particles is less than the range 1-10 μm, not more than the 10% of the total volume of particles is greater than the range 225-400 μm, and the d0.5 of the size distribution is in the range of about 40-200 μm, respectively.

The invention according to the above wherein the drug, and/or metabolite and/or prodrug is present as particles having a particle size distribution expressed as volume as follows: d0.9 is about 150 to about 400 μm, d0.5 is about 40 to about 200 μm and d0.1 is about 10 to about 60 μm.

The invention claimed is:

1. A method of treating schizophrenia or bipolar disorder, the method comprising administering a therapeutically effective amount of an injectable depot composition to a subject in need thereof, said injectable composition consisting of
   about 13% wt of drug which is risperidone and/or paliperidone or any pharmaceutically acceptable salt thereof in any combination; and
   a polymeric solution consisting of DMSO and biocompatible poly(lactide-co-glycolide) (PLGA) copolymer having a monomer ratio of lactic acid to glycolic acid of about 50:50 and an inherent viscosity in the range of 0.25-0.30 dl/g measured by gel permeation chromatography in tetrahydrofuran at 30° C. using a flow rate of 1 ml/min; wherein
   the mass ratio of polymeric solution to drug is about 6.5:1 to about 7:1; and
   the mass ratio of DMSO to drug is about 4:1 to about 5:1.

2. The method of claim 1, wherein said injectable composition is administered intramuscularly, intraperitoneally, intrathecally, intravaginally, subcutaneously, intracranially or intracerebrally.

3. The method of claim 1, wherein said injectable composition is administered every two weeks, every three weeks, every four weeks, or every five weeks during a treatment period.

4. The method of claim 1, wherein said injectable composition comprises about 25 mg to about 150 mg of said drug.

5. The method of claim 1, wherein after administration said injectable composition:
   a) provides an average plasma concentration of said drug that ranges from about 5 to about 80 ng/ml when about 116 to about 700 mg, respectively, of said injectable composition comprising about 25 mg to about 150 mg, respectively, of said drug are administered;
   b) provides an average plasma concentration of said drug that ranges from about 5 to about 150 ng/ml or from about 10 to about 100 ng/ml in the steady state during a dosing period;
   c) provides an average Cmin of said drug in the range of about 1-80 ng/ml, 5-50 ng/ml, or about 5-40 ng/ml when an amount of said injectable composition equivalent to a dose of about 25-150 mg, about 37.5-125 mg, or about 50-100 mg, respectively, of said drug is administered;
   d) provides an average Cmax of said drug in the range of about 8-300 ng/ml, 10-150 ng/ml, or 10-120 ng/ml when an amount of said injectable composition equivalent to a dose of 25-150 mg, 37.5-125 mg, or 50-100 mg, respectively, of said drug is administered; or
   e) provides therapeutic plasma levels of said drug from the first day to at least 14 days, at least 21 days, at least 28 days, at least 31 days, or at least 36 days after administration.

6. The method of claim 1, wherein said composition
   a) provides a plasma concentration profile of said drug that exhibits one, two or more maxima;
   b) provides a plasma concentration profile of said drug that exhibits one, two or more minima;
   c) provides a plasma concentration profile of said drug that exhibits a maximum during the initial one to six days, one to three days, or one to two days after administration;
   d) provides a plasma concentration profile of said drug that exhibits a maximum during 11 to 13 days or 12 to 14 days after administration;
   e) provides a plasma concentration profile of said drug that exhibits a maximum during 14 to 24 days of a 4-week dosing period; or
   f) provides a plasma concentration profile of said drug that is within ±20% of the average or mean plasma concentration during a dosing period.

7. The method of claim 1, wherein plural doses of said injectable composition are administered.

8. The method of claim 1 further comprising sterilizing said copolymer, said polymeric solution and/or said risperidone or paliperidone prior to administration.

9. The method of claim 8, wherein said sterilizing comprises exposure to a dose of beta-irradiation in the range of 5-25 KGy; or wherein said sterilizing comprises filtering said polymeric solution.

10. The method of claim 1, wherein said injectable composition releases 0.5% wt up to 20% wt of its charge of risperidone or paliperidone within 24 hours after being placed in an aqueous environment.

11. The method of claim 1, wherein the drug has a particle size distribution selected from the group consisting of
   a) not more than 10% of the total volume of the particles are smaller than 10 microns, and not more than 10% of the total volume of particles are greater than 225 microns;
   b) not more than 10% of the total volume of the particles is less than the range 1-10 μm, not more than 10% of the total volume of particles is greater than the range 225-400 μm, and the d0.5 of the size distribution is in the range of about 40-200 μm;
   c) expressed as volume, d0.9 is about 150 to about 400 μm, d0.5 is about 40 to about 200 μm and d0.1 is about 10 to about 60 μm;
   d) not more than 10% of the total volume of the particles is less than the range 0.1-10 μm, not more than the 10% of the total volume of particles is greater than the range 225-1000 μm, and the d0.5 of the size distribution is in the range of about 10-1000 μm;
   e) not more than 10% of the total volume of the particles is less than the range 0.5-10 μm, not more than the 10% of the total volume of particles is greater than the range 225-700 μm, and the d0.5 of the size distribution is in the range of about 20-700 μm;
   f) not more than 10% of the total volume of the particles is less than the range 1-10 μm, not more than the 10% of the total volume of particles is greater than the range 225-400 μm, and the d0.5 of the size distribution is in the range of about 40-200 μm;
   g) d0.1 of 27.49 microns, d0.5 of 79.9 microns, and d0.9 of 176.66 microns;
   h) d0.1 of 17.41 microns, d0.5 of 51.61 microns, and d0.9 of 175.32 microns; and
   i) d0.1 of ≤10 microns, d0.5 of 40-130 microns, and d0.9 of >225 microns.

12. The method of claim 1, wherein said monomer ratio ranges from 48:52 to 52:48.

13. A method of treating schizophrenia or bipolar disorder, the method comprising administering a therapeutically effective amount of an injectable depot composition to a subject in need thereof, said injectable composition consisting of about 13% wt of drug which is risperidone and/or paliperidone or any pharmaceutically acceptable salt thereof in any combination;
   DMSO; and
   biocompatible poly(lactide-co-glycolide) (PLGA) copolymer having a monomer ratio of lactic acid to glycolic acid of about 50:50 and an inherent viscosity in the range of 0.25-0.29 dl/g measured by gel permeation chromatography in tetrahydrofuran at 30° C. using a flow rate of 1 ml/min; wherein
   the mass ratio of drug to (polymer+drug) is about 33%, expressed as the percentage of the drug weight with respect to total weight of the drug plus polymer; and
   the mass ratio of DMSO to drug is about 4.66:1.

14. The method of claim 13, wherein said injectable composition is administered intramuscularly, intraperitoneally, intrathecally, intravaginally, subcutaneously, intracranially or intracerebrally.

15. The method of claim 13, wherein said injectable composition is administered every two weeks, every three weeks, every four weeks, or every five weeks during a treatment period.

16. The method of claim 13, wherein said injectable composition comprises about 25 mg to about 150 mg of said drug.

17. The method of claim 13, wherein after administration said injectable composition:
   a) provides an average plasma concentration of said drug that ranges from about 5 to about 80 ng/ml when about 116 to about 700 mg, respectively, of said injectable composition comprising about 25 mg to about 150 mg, respectively, of said drug are administered;

b) provides an average plasma concentration of said drug that ranges from about 5 to about 150 ng/ml or from about 10 to about 100 ng/ml in the steady state during a dosing period;

c) provides an average Cmin of said drug in the range of about 1-80 ng/ml, 5-50 ng/ml, or about 5-40 ng/ml when an amount of said injectable composition equivalent to a dose of about 25-150 mg, about 37.5-125 mg, or about 50-100 mg, respectively, of said drug is administered;

d) provides an average Cmax of said drug in the range of about 8-300 ng/ml, 10-150 ng/ml, or 10-120 ng/ml when an amount of said injectable composition equivalent to a dose of 25-150 mg, 37.5-125 mg, or 50-100 mg, respectively, of said drug is administered; or e) provides therapeutic plasma levels of said drug from the first day to at least 14 days, at least 21 days, at least 28 days, at least 31 days, or at least 36 days after administration.

18. The method of claim 13, wherein said composition
   a) provides a plasma concentration profile of said drug that exhibits one, two or more maxima;
   b) provides a plasma concentration profile of said drug that exhibits one, two or more minima;
   c) provides a plasma concentration profile of said drug that exhibits a maximum during the initial one to six days, one to three days, or one to two days after administration;
   d) provides a plasma concentration profile of said drug that exhibits a maximum during 11 to 13 days or 12 to 14 days after administration;
   e) provides a plasma concentration profile of said drug that exhibits a maximum during 14 to 24 days of a 4-week dosing period; or
   f) provides a plasma concentration profile of said drug that is within ±20% of the average or mean plasma concentration during a dosing period.

19. The method of claim 13, wherein plural doses of said injectable composition are administered.

20. The method of claim 13 further comprising sterilizing said copolymer, said polymeric solution and/or said risperidone or paliperidone prior to administration.

21. The method of claim 20, wherein said sterilizing comprises exposure to a dose of beta-irradiation in the range of 5-25 KGy; or wherein said sterilizing comprises filtering said polymeric solution.

22. The method of claim 13, wherein said injectable composition releases 0.5% wt up to 20% wt of its charge of risperidone or paliperidone within 24 hours after being placed in an aqueous environment.

23. The method of claim 13, wherein the drug has a particle size distribution selected from the group consisting of
   a) not more than 10% of the total volume of the particles are smaller than 10 microns, and not more than 10% of the total volume of particles are greater than 225 microns;
   b) not more than 10% of the total volume of the particles is less than the range 1-10 µm, not more than 10% of the total volume of particles is greater than the range 225-400 µm, and the d0.5 of the size distribution is in the range of about 40-200 µm;
   c) expressed as volume, d0.9 is about 150 to about 400 µm, d0.5 is about 40 to about 200 µm and d0.1 is about 10 to about 60 µm;
   d) not more than 10% of the total volume of the particles is less than the range 0.1-10 µm, not more than 10% of the total volume of particles is greater than the range 225-1000 µm, and the d0.5 of the size distribution is in the range of about 10-1000 µm;
   e) not more than 10% of the total volume of the particles is less than the range 0.5-10 µm, not more than 10% of the total volume of particles is greater than the range 225-700 µm, and the d0.5 of the size distribution is in the range of about 20-700 µm;
   f) not more than 10% of the total volume of the particles is less than the range 1-10 µm, not more than 10% of the total volume of particles is greater than the range 225-400 µm, and the d0.5 of the size distribution is in the range of about 40-200 µm;
   g) d0.1 of 27.49 microns, d0.5 of 79.9 microns, and d0.9 of 176.66 microns;
   h) d0.1 of 17.41 microns, d0.5 of 51.61 microns, and d0.9 of 175.32 microns; and
   i) d0.1 of ≤10 microns, d0.5 of 40-130 microns, and d0.9 of >225 microns.

24. The method of claim 13, wherein said monomer ratio ranges from 48:52 to 52:48.

25. A method of treating schizophrenia or bipolar disorder, the method comprising administering a therapeutically effective amount of an injectable depot composition to a subject in need thereof, said injectable composition consisting of
   about 13% wt of drug which is risperidone and/or paliperidone or any pharmaceutically acceptable salt thereof in any combination;
   DMSO; and
   25-27% wt of biocompatible poly(lactide-co-glycolide) (PLGA) copolymer having a monomer ratio of lactic acid to glycolic acid of about 50:50 and an inherent viscosity in the range of 0.25-0.30 dl/g measured by gel permeation chromatography in tetrahydrofuran at 30° C. using a flow rate of 1 ml/min; wherein
   the mass ratio of DMSO to drug is about 4:1 to about 5:1.

26. The method of claim 25, wherein said injectable composition is administered intramuscularly, intraperitoneally, intrathecally, intravaginally, subcutaneously, intracranially or intracerebrally.

27. The method of claim 25, wherein said injectable composition is administered every two weeks, every three weeks, every four weeks, or every five weeks during a treatment period.

28. The method of claim 25, wherein said injectable composition comprises about 25 mg to about 150 mg of said drug.

29. The method of claim 25, wherein after administration said injectable composition
   a) provides an average plasma concentration of said drug that ranges from about 5 to about 80 ng/ml when about 116 to about 700 mg, respectively, of said injectable composition comprising about 25 mg to about 150 mg, respectively, of said drug are administered;
   b) provides an average plasma concentration of said drug that ranges from about 5 to about 150 ng/ml or from about 10 to about 100 ng/ml in the steady state during a dosing period;
   c) provides an average Cmin of said drug in the range of about 1-80 ng/ml, 5-50 ng/ml, or about 5-40 ng/ml when an amount of said injectable composition equivalent to a dose of about 25-150 mg, about 37.5-125 mg, or about 50-100 mg, respectively, of said drug is administered;
   d) provides an average Cmax of said drug in the range of about 8-300 ng/ml, 10-150 ng/ml, or 10-120 ng/ml when an amount of said injectable composition equivalent to a dose of 25-150 mg, 37.5-125 mg, or 50-100 mg, respectively, of said drug is administered; or
e) provides therapeutic plasma levels of said drug from the first day to at least 14 days, at least 21 days, at least 28 days, at least 31 days, or at least 36 days after administration.

30. The method of claim 25, wherein said injectable composition
a) provides a plasma concentration profile of said drug that exhibits one, two or more maxima;
b) provides a plasma concentration profile of said drug that exhibits one, two or more minima;
c) provides a plasma concentration profile of said drug that exhibits a maximum during the initial one to six days, one to three days, or one to two days after administration;
d) provides a plasma concentration profile of said drug that exhibits a maximum during 11 to 13 days or 12 to 14 days after administration;
e) provides a plasma concentration profile of said drug that exhibits a maximum during 14 to 24 days of a 4-week dosing period; or
f) provides a plasma concentration profile of said drug that is within ±20% of the average or mean plasma concentration during a dosing period.

31. The method of claim 25, wherein plural doses of said injectable composition are administered.

32. The method of claim 25 further comprising sterilizing said copolymer, said polymeric solution and/or said risperidone or paliperidone prior to administration.

33. The method of claim 32, wherein said sterilizing comprises exposure to a dose of beta-irradiation in the range of 5-25 KGy; or wherein said sterilizing comprises filtering said polymeric solution.

34. The method of claim 25, wherein said injectable composition releases 0.5% wt up to 20% wt of its charge of risperidone or paliperidone within 24 hours after being placed in an aqueous environment.

35. The method of claim 25, wherein the drug has a particle size distribution selected from the group consisting of
a) not more than 10% of the total volume of the particles are smaller than 10 microns, and not more than 10% of the total volume of particles are greater than 225 microns;
b) not more than 10% of the total volume of the particles is less than the range 1-10 µm, not more than 10% of the total volume of particles is greater than the range 225-400 µm, and the d0.5 of the size distribution is in the range of about 40-200 µm;
c) expressed as volume, d0.9 is about 150 to about 400 µm, d0.5 is about 40 to about 200 µm and d0.1 is about 10 to about 60 µm;
d) not more than 10% of the total volume of the particles is less than the range 0.1-10 µm, not more than 10% of the total volume of particles is greater than the range 225-1000 µm, and the d0.5 of the size distribution is in the range of about 10-1000 µm;
e) not more than 10% of the total volume of the particles is less than the range 0.5-10 µm, not more than 10% of the total volume of particles is greater than the range 225-700 µm, and the d0.5 of the size distribution is in the range of about 20-700 µm;
f) not more than 10% of the total volume of the particles is less than the range 1-10 µm, not more than 10% of the total volume of particles is greater than the range 225-400 µm, and the d0.5 of the size distribution is in the range of about 40-200 µm;
g) d0.1 of 27.49 microns, d0.5 of 79.9 microns, and d0.9 of 176.66 microns;
h) d0.1 of 17.41 microns, d0.5 of 51.61 microns, and d0.9 of 175.32 microns; and
i) d0.1 of ≤10 microns, d0.5 of 40-130 microns, and d0.9 of >225 microns.

36. The method of claim 25, wherein said monomer ratio ranges from 48:52 to 52:48.

37. A method of treating schizophrenia or bipolar disorder, the method comprising administering a therapeutically effective amount of an injectable depot composition to a subject in need thereof, said subject an injectable composition consisting of about 13% wt of drug which is risperidone and/or paliperidone or any pharmaceutically acceptable salt thereof in any combination;
DMSO; and
25-27% wt of biocompatible poly(lactide-co-glycolide) (PLGA) copolymer having a monomer ratio of lactic acid to glycolic acid of about 50:50 and a molecular weight in the range of 28-43 kDa; wherein
the mass ratio of DMSO to drug is about 4:1 to about 5:1.

38. The method of claim 37, wherein said copolymer has molecular weight in the range of 30-36 kDa.

39. The method of claim 37, wherein said injectable composition is administered intramuscularly, intraperitoneally, intrathecally, intravaginally, subcutaneously, intracranially or intracerebrally.

40. The method of claim 37, wherein said injectable composition is administered every two weeks, every three weeks, every four weeks, or every five weeks during a treatment period.

41. The method of claim 37, wherein said injectable composition comprises about 25 mg to about 150 mg of said drug.

42. The method of claim 37, wherein after administration said injectable composition:
a) provides an average plasma concentration of said drug that ranges from about 5 to about 80 ng/ml when about 116 to about 700 mg, respectively, of said injectable composition comprising about 25 mg to about 150 mg, respectively, of said drug are administered;
b) provides an average plasma concentration of said drug that ranges from about 5 to about 150 ng/ml or from about 10 to about 100 ng/ml in the steady state during a dosing period;
c) provides an average Cmin of said drug in the range of about 1-80 ng/ml, 5-50 ng/ml, or about 5-40 ng/ml when an amount of said injectable composition equivalent to a dose of about 25-150 mg, about 37.5-125 mg, or about 50-100 mg, respectively, of said drug is administered;
d) provides an average Cmax of said drug in the range of about 8-300 ng/ml, 10-150 ng/ml, or 10-120 ng/ml when an amount of said injectable composition equivalent to a dose of 25-150 mg, 37.5-125 mg, or 50-100 mg, respectively, of said drug is administered; or
e) provides therapeutic plasma levels of said drug from the first day to at least 14 days, at least 21 days, at least 28 days, at least 31 days, or at least 36 days after administration.

43. The method of claim 37, wherein said injectable composition
a) provides a plasma concentration profile of said drug that exhibits one, two or more maxima;

b) provides a plasma concentration profile of said drug that exhibits one, two or more minima;

c) provides a plasma concentration profile of said drug that exhibits a maximum during the initial one to six days, one to three days, or one to two days after administration;

d) provides a plasma concentration profile of said drug that exhibits a maximum during 11 to 13 days or 12 to 14 days after administration;

e) provides a plasma concentration profile of said drug that exhibits a maximum during 14 to 24 days of a 4-week dosing period; or f) provides a plasma concentration profile of said drug that is within ±20% of the average or mean plasma concentration during a dosing period.

44. The method of claim 37, wherein plural doses of said injectable composition are administered.

45. The method of claim 37 further comprising sterilizing said copolymer, said polymeric solution and/or said risperidone or paliperidone prior to administration.

46. The method of claim 45, wherein said sterilizing comprises exposure to a dose of beta-irradiation in the range of 5-25 KGy; or wherein said sterilizing comprises filtering said polymeric solution.

47. The method of claim 37, wherein said injectable composition releases 0.5% wt up to 20% wt of its charge of risperidone or paliperidone within 24 hours after being placed in an aqueous environment.

48. The method of claim 37, wherein the drug has a particle size distribution selected from the group consisting of a) not more than 10% of the total volume of the particles are smaller than 10 microns, and not more than 10% of the total volume of particles are greater than 225 microns;

b) not more than 10% of the total volume of the particles is less than the range 1-10 μm, not more than 10% of the total volume of particles is greater than the range 225-400 μm, and the d0.5 of the size distribution is in the range of about 40-200 μm;

c) expressed as volume, d0.9 is about 150 to about 400 μm, d0.5 is about 40 to about 200 μm and d0.1 is about 10 to about 60 μm;

d) not more than 10% of the total volume of the particles is less than the range 0.1-10 μm, not more than the 10% of the total volume of particles is greater than the range 225-1000 μm, and the d0.5 of the size distribution is in the range of about 10-1000 μm;

e) not more than 10% of the total volume of the particles is less than the range 0.5-10 μm, not more than the 10% of the total volume of particles is greater than the range 225-700 μm, and the d0.5 of the size distribution is in the range of about 20-700 μm;

f) not more than 10% of the total volume of the particles is less than the range 1-10 μm, not more than the 10% of the total volume of particles is greater than the range 225-400 μm, and the d0.5 of the size distribution is in the range of about 40-200 μm;

g) d0.1 of 27.49 microns, d0.5 of 79.9 microns, and d0.9 of 176.66 microns;

h) d0.1 of 17.41 microns, d0.5 of 51.61 microns, and d0.9 of 175.32 microns; and i) d0.1 of ≤10 microns, d0.5 of 40-130 microns, and d0.9 of >225 microns.

49. The method of claim 37, wherein said monomer ratio ranges from 48:52 to 52:48.

* * * * *